(12) United States Patent
Namkoong et al.

(10) Patent No.: US 7,698,072 B2
(45) Date of Patent: Apr. 13, 2010

(54) METHOD FOR QUANTIFYING INITIAL CONCENTRATION OF NUCLEIC ACID FROM REAL-TIME NUCLEIC ACID AMPLIFICATION DATA

(75) Inventors: Kak Namkoong, Seoul (KR); Jin-tae Kim, Gyeonggi-do (KR); Young-sun Lee, Gyeonggi-do (KR); Young-a Kim, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 1088 days.

(21) Appl. No.: 11/217,694

(22) Filed: Sep. 1, 2005

(65) Prior Publication Data

US 2006/0047443 A1 Mar. 2, 2006

(30) Foreign Application Priority Data

Sep. 1, 2004 (KR) ............... 10-2004-0069560
Apr. 13, 2005 (KR) ............... 10-2005-0030745

(51) Int. Cl.
*G06F 19/00* (2006.01)
(52) U.S. Cl. ............................................. 702/20
(58) Field of Classification Search ............... 702/20
See application file for complete search history.

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 6,303,305 B1 | 10/2001 | Wittwer et al. | 435/6 |
| 6,503,720 B2 | 1/2003 | Wittwer et al. | 435/6 |
| 2002/0028452 A1 | 3/2002 | Witter et al. | |
| 2002/0031768 A1 | 3/2002 | McMillan et al. | 435/6 |
| 2003/0165832 A1 | 9/2003 | Sagner et al. | |

OTHER PUBLICATIONS

Wilhelm et al., "SoFAR: Software for Fully Automatic Evaluation of Real-Time PCR Data," BioTechniques (2003) vol. 34, pp. 324-332.*
Extended European Search Report on EP 05019029.7-2405.
Chinese Office Action; Jun. 22, 2007; 200510098030.1.
European Office Action; Jul. 13, 2007; 07010827.9-1222.
All the references cited in the Search Report and not previously submitted are listed above, Aug. 27, 2007.

* cited by examiner

*Primary Examiner*—Jerry Lin
(74) *Attorney, Agent, or Firm*—Cantor Colburn LLP

(57) ABSTRACT

Provided is a method for quantifying an initial concentration of a nucleic acid from a real-time nucleic acid amplification data. Nucleic acid (DNA or RNA) extracted from organism or virus is amplified using an enzyme. Then, the initial concentration of the nucleic acid is found by calculating the characteristic amplification cycle number or the characteristic amplification time at which the fluorescence intensity of the nucleic acid subtracted by the background fluorescence intensity of the nucleic acid has half of its maximum value, or the characteristic amplification cycle number or the characteristic amplification time at which the amplification efficiency has the maximum or the minimum value, or the prior-to-amplification fluorescence intensity of the nucleic acid subtracted by the background fluorescence intensity of the nucleic acid. Accordingly, the initial concentration of the nucleic acid can be calculated without differentiation or integration.

7 Claims, 22 Drawing Sheets

FIG. 7A

| Run Number | copy/rxn | Ct | n,0.5 | Log(R0) | n,Emax | VALUE(Ct) OF Y AT X=0 | SLOPE(Ct) | r^2 (%) | VALUE OF Y AT X=0 (n,0.5) | SLOPE (n,0.5) | r^2 (%) | VALUE OF Y AT X=0 (Log(R0)) | SLOPE (Log(R0)) | r^2 (%) | VALUE OF Y AT X=0 (n,Emax) | SLOPE (n,Emax) | r^2 (%) |
|---|---|---|---|---|---|---|---|---|---|---|---|---|---|---|---|---|---|
| 1 | 1.0E+04 | 28.476 | 32.219 | -5.193 | 27.593 | 40.989 | -3.683 | 99.900 | 46.057 | -3.681 | 100.000 | -0.027 | 0.749 | 96.100 | 41.064 | -3.410 | 99.900 |
| | 1.0E+05 | 22.470 | 28.347 | -4.077 | 23.849 | | | | | | | | | | | | |
| | 1.0E+06 | 19.020 | 24.755 | -3.704 | 20.818 | | | | | | | | | | | | |
| | 1.0E+07 | 15.410 | 21.142 | -2.860 | 17.245 | | | | | | | | | | | | |
| 2 | 1.0E+04 | 25.960 | 31.343 | -4.361 | 27.153 | 40.247 | -3.554 | 99.900 | 46.214 | -3.556 | 99.800 | -7.542 | 0.694 | 99.900 | 40.437 | -3.302 | 99.900 |
| | 1.0E+05 | 22.510 | 28.559 | -4.033 | 23.959 | | | | | | | | | | | | |
| | 1.0E+06 | 19.070 | 25.054 | -3.456 | 20.776 | | | | | | | | | | | | |
| | 1.0E+07 | 15.260 | 21.154 | -2.774 | 17.206 | | | | | | | | | | | | |
| 3 | 1.0E+04 | 25.510 | 31.053 | -4.657 | 26.658 | 39.621 | -3.477 | 99.700 | 45.975 | -3.634 | 99.500 | -7.002 | 0.598 | 99.400 | 39.644 | -3.198 | 99.500 |
| | 1.0E+05 | 22.260 | 28.429 | -3.947 | 23.812 | | | | | | | | | | | | |
| | 1.0E+06 | 19.020 | 25.095 | -3.404 | 20.718 | | | | | | | | | | | | |
| | 1.0E+07 | 15.100 | 20.988 | -2.945 | 17.026 | | | | | | | | | | | | |
| 4 | 1.0E+04 | 25.170 | 31.175 | -4.647 | 26.274 | 38.568 | -3.287 | 99.400 | 45.068 | -3.376 | 98.700 | -6.981 | 0.595 | 99.300 | 38.695 | -3.027 | 98.900 |
| | 1.0E+05 | 22.430 | 28.843 | -3.929 | 23.841 | | | | | | | | | | | | |
| | 1.0E+06 | 18.990 | 24.899 | -3.439 | 20.724 | | | | | | | | | | | | |
| | 1.0E+07 | 16.390 | 21.135 | -2.829 | 17.256 | | | | | | | | | | | | |
| 5 | 1.0E+04 | 25.410 | 31.500 | -4.820 | 26.699 | 38.949 | -3.358 | 99.800 | 45.512 | -3.455 | 99.500 | -6.915 | 0.598 | 99.300 | 39.270 | -3.127 | 99.700 |
| | 1.0E+05 | 22.230 | 28.368 | -3.913 | 23.950 | | | | | | | | | | | | |
| | 1.0E+06 | 18.890 | 25.071 | -3.410 | 20.727 | | | | | | | | | | | | |
| | 1.0E+07 | 15.300 | 21.078 | -2.838 | 17.222 | | | | | | | | | | | | |
| 6 | 1.0E+04 | 25.650 | 31.945 | -4.600 | 26.565 | 39.596 | -3.470 | 99.960 | 46.764 | -3.651 | 99.500 | -6.813 | 0.570 | 98.600 | 39.380 | -3.167 | 99.600 |
| | 1.0E+05 | 22.270 | 28.765 | -3.871 | 23.758 | | | | | | | | | | | | |
| | 1.0E+06 | 18.820 | 25.108 | -3.373 | 20.663 | | | | | | | | | | | | |
| | 1.0E+07 | 15.200 | 20.984 | -2.868 | 17.109 | | | | | | | | | | | | |

FIG. 7B

| Run number | copy/rxn | Ct | n_0.5 | Log[R0] | n_Emax | copy/rxn(Ct) | copy/rxn(n_0.5) | copy/rxn(Log[R0]) | copy/rxn(n_Emax) | Error(Ct) | Error(n_0.5) | Error(Log[R0]) | Error(n_Emax) |
|---|---|---|---|---|---|---|---|---|---|---|---|---|---|
| 1 | 5.00E+05 | 19.990 | 25.743 | -3.749 | 21.541 | 5.40E+05 | 5.45E+05 | 6.01E+05 | 5.32E+05 | 8.08% | 9.08% | 20.23% | 6.37% |
|   | 2.50E+06 | 17.150 | 22.914 | -3.349 | 18.849 | 3.22E+06 | 3.20E+06 | 2.09E+06 | 3.28E+06 | 28.86% | 28.09% | 16.41% | 31.09% |
| 2 | 5.00E+05 | 19.990 | 25.692 | -3.780 | 21.623 | 5.01E+05 | 5.90E+05 | 3.17E+05 | 4.98E+05 | 0.19% | 17.96% | 36.54% | 0.47% |
|   | 2.50E+06 | 17.030 | 23.177 | -3.061 | 18.925 | 3.41E+06 | 3.01E+06 | 3.57E+06 | 3.27E+06 | 36.38% | 20.23% | 42.72% | 30.63% |
| 3 | 5.00E+05 | 19.900 | 25.801 | -3.848 | 21.622 | 4.70E+05 | 5.12E+05 | 4.07E+05 | 4.31E+05 | 6.06% | 2.43% | 18.67% | 13.76% |
|   | 2.50E+06 | 17.080 | 23.172 | -3.090 | 18.897 | 3.08E+06 | 2.84E+06 | 3.49E+06 | 3.07E+06 | 23.23% | 13.60% | 39.64% | 22.72% |
| 4 | 5.00E+05 | 19.840 | 25.629 | -3.645 | 21.447 | 4.98E+05 | 5.68E+05 | 4.07E+05 | 5.00E+05 | 0.46% | 13.59% | 18.59% | 0.01% |
|   | 2.50E+06 | 17.020 | 23.177 | -3.058 | 18.885 | 3.59E+06 | 3.02E+06 | 3.85E+06 | 3.51E+06 | 43.54% | 20.94% | 57.83% | 40.52% |
| 5 | 5.00E+05 | 19.960 | 25.703 | -3.766 | 21.610 | 4.52E+05 | 5.39E+05 | 2.39E+05 | 4.44E+05 | 9.65% | 7.83% | 52.26% | 11.30% |
|   | 2.50E+06 | 17.010 | 23.153 | -3.067 | 18.876 | 3.41E+06 | 2.95E+06 | 3.74E+06 | 3.32E+06 | 36.59% | 17.95% | 49.61% | 32.82% |
| 6 | 5.00E+05 | 19.770 | 25.482 | -3.681 | 21.436 | 5.17E+05 | 6.78E+05 | 3.11E+05 | 4.86E+05 | 3.34% | 35.67% | 37.73% | 2.77% |
|   | 2.50E+06 | 16.970 | 23.356 | -3.002 | 18.820 | 3.31E+06 | 2.61E+06 | 4.84E+06 | 3.28E+06 | 32.51% | 4.41% | 83.41% | 31.04% |

FIG. 7C

|  | Error(Ct) | Error(n_0.5) | Error(Log[R0]) | Error(n_E max) |
|---|---|---|---|---|
| Avg error at 5.0E5 | 4.63% | 14.43% | 30.67% | 5.78% |
| Avg error at 2.5E6 | 33.51% | 17.53% | 49.93% | 31.47% |
| StDev error at 5.0E5 | 3.95% | 11.67% | 13.78% | 5.75% |
| StDev error at 2.5E6 | 7.02% | 7.96% | 25.44% | 5.68% |

WITHOUT BACKGROUND FLUORESCENCE
INTENSITY CORRECTION

| copy/rxn | Average(nEmax) | St.Dev.(nEmax) | %CV of nEmax |
|---|---|---|---|
| 1.00E+08 | 3.458E+00 | 3.314E-01 | 9.58% |
| 1.00E+07 | 1.183E+01 | 7.115E-01 | 6.02% |
| 1.00E+06 | 1.502E+01 | 1.040E+00 | 6.92% |
| 1.00E+05 | 1.896E+01 | 1.740E+00 | 9.18% |
| 1.00E+04 | 2.152E+01 | 1.611E+00 | 7.49% |
| 1.00E+03 | 2.556E+01 | 3.020E+00 | 11.82% |
| 1.00E+02 | 3.225E+01 | 6.556E+00 | 20.33% |
| 1.00E+01 | 3.101E+01 | 5.792E+00 | 18.68% |
| 1.00E+00 | 3.484E+01 | 1.325E+01 | 38.03% |

WITHOUT BACKGROUND FLUORESCENCE
INTENSITY CORRECTION

| copy/rxn | Average(nEmax) | St.Dev.(nEmax) | %CV of nEmax |
|---|---|---|---|
| 1.00E+08 | 1.32E+01 | 1.576E-01 | 1.19% |
| 1.00E+07 | 1.655E+01 | 1.381E-01 | 0.83% |
| 1.00E+06 | 2.040E+01 | 2.441E-01 | 1.20% |
| 1.00E+05 | 2.412E+01 | 2.726E-01 | 1.13% |
| 1.00E+04 | 2.770E+01 | 2.999E-01 | 1.08% |
| 1.00E+03 | 3.164E+01 | 1.246E+00 | 3.94% |
| 1.00E+05 | 3.435E+01 | 7.591E+00 | 22.10% |
| 1.00E+04 | 3.821E+01 | 6.954E+00 | 18.20% |
| 1.00E+03 | 3.033E+01 | 1.747E+01 | 57.60% |

METHOD FOR QUANTIFYING INITIAL CONCENTRATION OF NUCLEIC ACID FROM REAL-TIME NUCLEIC ACID AMPLIFICATION DATA

This application claims the priority of Korean Patent Application Nos. 10-2004-0069560 and 10-2005-0030745, filed on Sep. 1, 2004 and Apr. 13, 2005, in the Korean Intellectual Property Office, the disclosure of which is incorporated herein in its entirety by reference.

BACKGROUND OF THE INVENTION

1. Field of the Invention

The present invention relates to a method for quantifying the initial nucleic acid concentration, and more particularly, to a method for quantifying the initial nucleic acid concentration from real-time nucleic acid amplification data, which is obtained by polymerase chain reaction (PCR), ligase chain reaction (LCR), strand displacement amplification (SDA), nucleic acid sequence-based amplification (NASBA), transcription mediated amplification (TMA), rolling-circle amplification (RCA), and so on.

2. Description of the Related Art

Polymerase chain reaction (PCR) is most widely used among a variety of analysis methods for detecting and quantifying nucleic acid. A principle of the PCR is disclosed in U.S. Pat. Nos. 4,683,195 and 4,683,202.

Conventional PCR gives only a qualitative result of an amplified DNA at end point by an agarose gel. However, such conventional PCR has a problem in that it cannot be used in quantitative analyses. In order to solve the problem, real-time PCR has been developed. The real-time PCR uses an optical detection system to detect in real time the fluorescence intensity that is proportional to the concentration of an amplified DNA, such that a quantitative analysis of DNA is possible.

Conventional methods for quantifying the initial concentration of a nucleic acid from a nucleic acid amplification data are disclosed in U.S. Pat. Nos. 6,303,305 and 6,503,720. In these conventional methods, a nucleic acid is amplified and a function representing the amount of the nucleic acid in each amplification cycle is obtained. Then, n-th order derivative of the function is calculated and the initial concentration of the nucleic acid is calculated from the result. Also, a quantitative analysis method using the maximum value of the derivative as threshold cycle (Ct) is disclosed in U.S. Pat. No. 6,303,305, and a quantitative analysis method using maximum, minimum and zero value of the derivative as Ct is disclosed in U.S. Pat. No. 6,503,720.

Also, another method for quantifying the initial concentration of a nucleic acid from the nucleic acid amplification data is disclosed in U.S. Patent Application Publication No. 2002-0031768. Herein, the concentration of the nucleic acid is quantified using a specific value of the derivative.

SUMMARY OF THE INVENTION

The present invention provides a method for quantifying the initial concentration of a nucleic acid from real-time nucleic acid amplification data without differentiation or integration.

According to an aspect of the present invention, a method for quantifying the initial concentration of a nucleic acid includes: amplifying a nucleic acid; producing a function representing a correlation between fluorescence intensity which increases or decreases in proportion to the amount of the nucleic acid and amplification cycle number or amplification time; using the function to calculate a characteristic amplification cycle number or a characteristic amplification time at which the fluorescence intensity of the nucleic acid subtracted by the background fluorescence intensity of the nucleic acid has half of its maximum value; and calculating the initial concentration of the nucleic acid from the characteristic amplification cycle number or the characteristic amplification time.

According to another aspect of the present invention, a method for quantifying the initial concentration of a nucleic acid includes: amplifying a nucleic acid; producing a function representing a correlation between fluorescence intensity which is proportional to the amount of the nucleic acid and amplification cycle number or amplification time of the nucleic acid; using the function to calculate the prior-to-amplification fluorescence intensity of the nucleic acid subtracted by a background fluorescence intensity of the nucleic acid; and calculating the initial concentration of the nucleic acid from the calculated prior-to-amplification fluorescence intensity subtracted by a background fluorescence intensity.

According to a further another aspect of the present invention, a method for quantifying the initial concentration of a nucleic acid includes: amplifying a nucleic acid; producing a function representing a correlation between the amplification efficiency of the nucleic acid and amplification cycle number or amplification time of the nucleic acid; using the function to calculate a characteristic amplification cycle number or a characteristic amplification time at which amplification efficiency has the maximum or the minimum value; and calculating the initial concentration of the nucleic acid from the characteristic amplification cycle number or the characteristic amplification time.

According to the present invention, the initial concentration of the nucleic acid can be quantified without differentiation or integration.

BRIEF DESCRIPTION OF THE DRAWINGS

The above and other features and advantages of the present invention will become more apparent by describing in detail exemplary embodiments thereof with reference to the attached drawings in which:

FIGS. 7A through 7C are tables showing the method for calculating the initial concentration of the nucleic acid according to the present invention and the result of the prior art;

DETAILED DESCRIPTION OF THE INVENTION

A method for quantifying the initial concentration of a nucleic acid from a real-time nucleic acid amplification data, especially, a PCR data will now be described with reference to the accompanying drawings.

Figure 1:
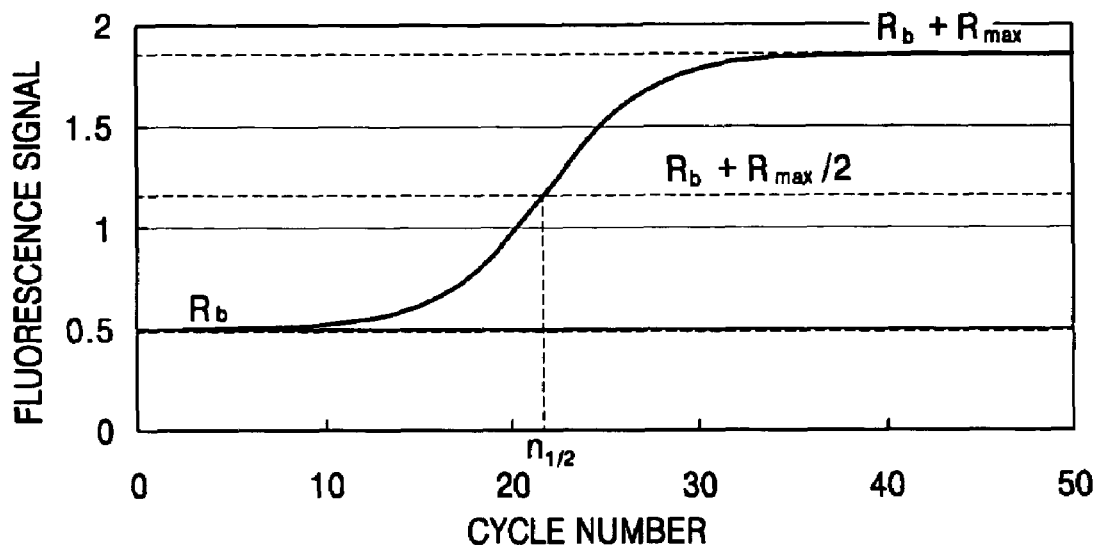
FIG. 1 is a graph showing a mathematical model of a correlation between the fluorescence intensity of the amplified nucleic acid and amplification cycle number.

FIG. 1 is a graph showing a mathematical model of the relation between the fluorescence intensity of the amplified nucleic acid and amplification cycle number.

Nucleic acid amplification using enzyme is performed by [a] methods requiring a thermal cycle, such as PCR, RT-PCR, nested PCR and LCR, or isothermal nucleic acid amplification methods, such as SDA, NASBA, TMA and RCA. Here, the nucleic acid may be extracted from an organism or a virus.

The result of measuring the fluorescence intensity of the nucleic acid at each amplification cycle from a real-time PCR experiment can be modelled as the graph shown in FIG. 1. A sigmoidal model of FIG. 1 can be expressed by Equation 1 below.

$$R = R_b + \frac{R_{max}}{1+e^{-\frac{n-n_{1/2}}{k}}} \quad \text{[Equation 1]}$$

where,
R: fluorescence intensity of a nucleic acid
$R_b$: background fluorescence intensity of a nucleic acid
$R_{max}$: the maximum fluorescence intensity of a nucleic acid
n: amplification cycle number
$n_{1/2}$: characteristic amplification cycle number at which the fluorescence intensity of the nucleic acid subtracted by the background fluorescence intensity of the nucleic acid has half of its maximum value
k: a parameter related to the rate of change of the fluorescence intensity during amplification reaction The error between the mathematical model and the actual PCR data can be calculated by Equation 2 below.

$$\varepsilon^2 = \sum_n \left[ R_n - \left\{ R_b + \frac{R_{max}}{1+e^{-\frac{(n-n_{1/2})}{k}}} \right\} \right]^2 \quad \text{[Equation 2]}$$

where $R_n$ represents the actual fluorescence intensity of a nucleic acid at n-th amplification cycle in real-time PCR.

Using the least-square fitting method in order to compute the parameters $R_b$, $R_{max}$, $n_{1/2}$ and k in the mathematical model of FIG. 1, nonlinear-equation set of Equation 3 or Equations 4a through 4d is obtained and this can be solved using the Newton-Raphson method.

$$\frac{\partial \varepsilon^2}{\partial R_b}=0, \frac{\partial \varepsilon^2}{\partial R_{max}}, \frac{\partial \varepsilon^2}{\partial n_{1/2}}=0, \frac{\partial \varepsilon^2}{\partial k}=0 \quad \text{[Equation 3]}$$

$$\sum_n \left[ R_n - \left\{ R_b + \frac{R_{max}}{1+e^{-\frac{(n-n_{1/2})}{k}}} \right\} \right]^2 = 0 \quad \text{[Equation 4a]}$$

-continued $$\sum_n \left[ R_n - \left\{ R_b - \frac{R_{max}}{1+e^{-\frac{(n-n_{1/2})}{k}}} \right\} \times \frac{1}{1+e^{-\frac{n-n_{1/2}}{k}}} \right] = 0 \quad \text{[Equation 4b]}$$

$$\sum_n \left[ R_n - \left\{ R_b + \frac{R_{max}}{1+e^{-\frac{(n-n_{1/2})}{k}}} \right\} \times \frac{e^{-\frac{n-n_{1/2}}{k}}}{\left\{1+e^{-\frac{n-n_{1/2}}{k}}\right\}^2} \right] = 0 \quad \text{[Equation 4c]}$$

$$\sum_n \left[ R_n - \left\{ R_b - \frac{R_{max}}{1+e^{-\frac{(n-n_{1/2})}{k}}} \right\} \times \frac{(n-n_{1/2})e^{-\frac{n-n_{1/2}}{k}}}{\left\{1+e^{-\frac{n-n_{1/2}}{k}}\right\}^2} \right] = 0 \quad \text{[Equation 4d]}$$

When n=0 in Equation 1, the fluorescence intensity of the nucleic acid before the amplification reaction subtracted by the background fluorescence intensity $R_b$ can be defined by Equation 5.

$$R_0 = \frac{R_{max}}{1+e^{n_{1/2}/k}} \quad \text{[Equation 5]}$$

FIGS. 2A through 2F are graphs showing the real amplification data of a HBV plasmid DNA and the least-square fitting results of those data with the mathematical model of FIG. 1.

Figure 2A:
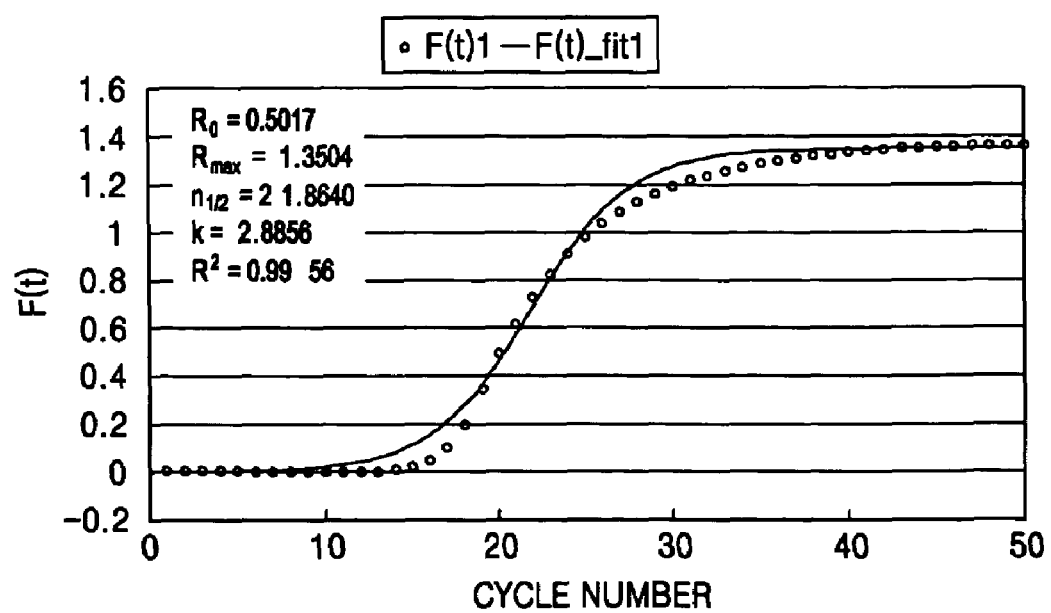
FIGS. 2A through 2F are graphs showing the real amplification data of a nucleic acid and the least-square fitting results of those data with the mathematical model of FIG. 1.
Figure 2B:
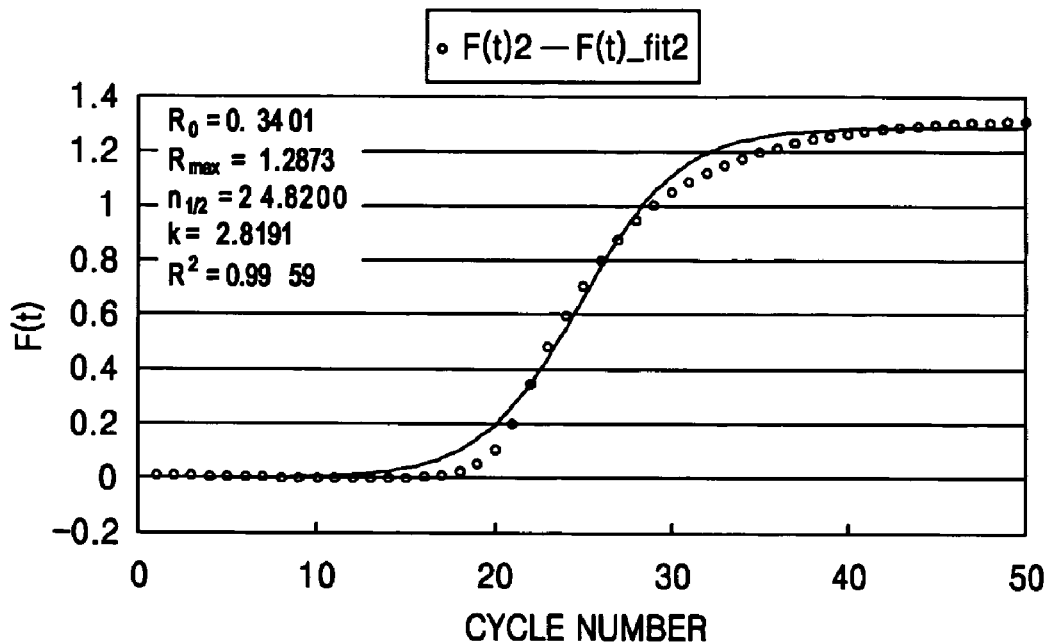
Figure 2C:
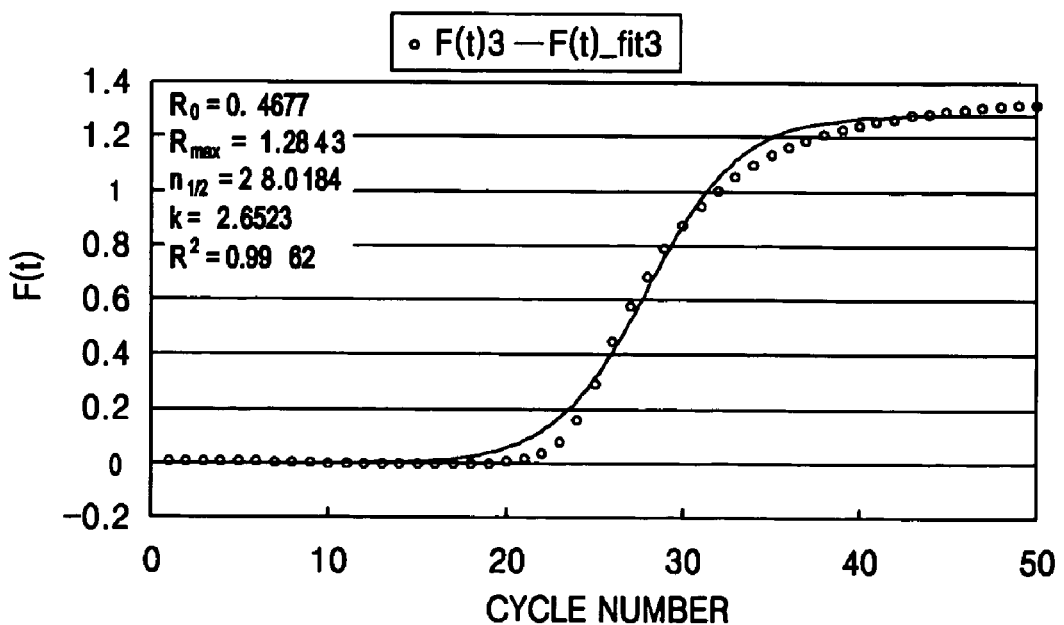
Figure 2D:
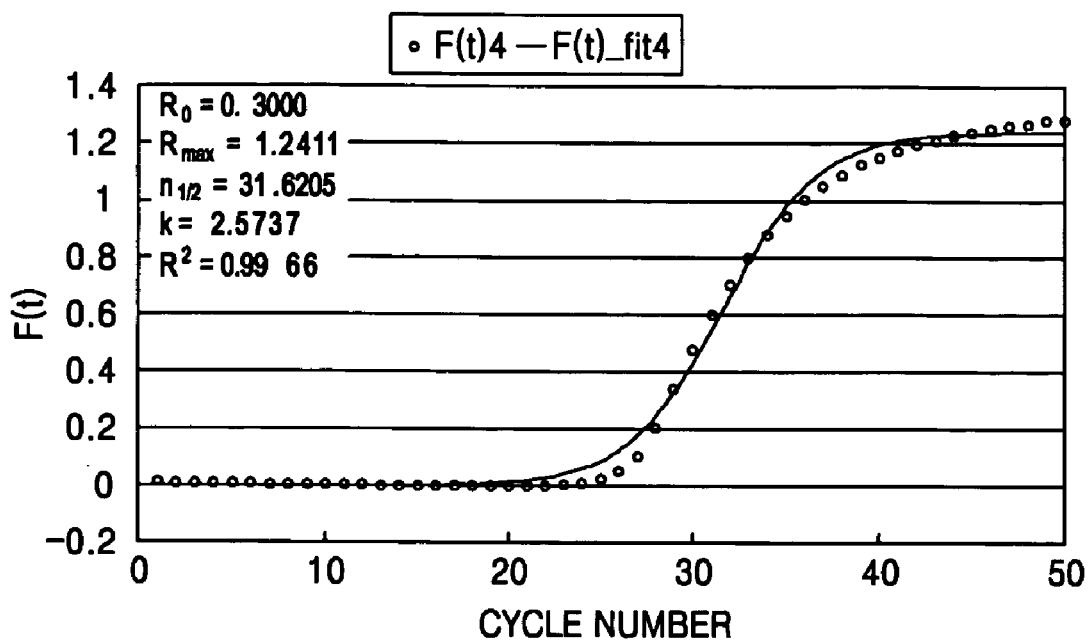
Figure 2E:
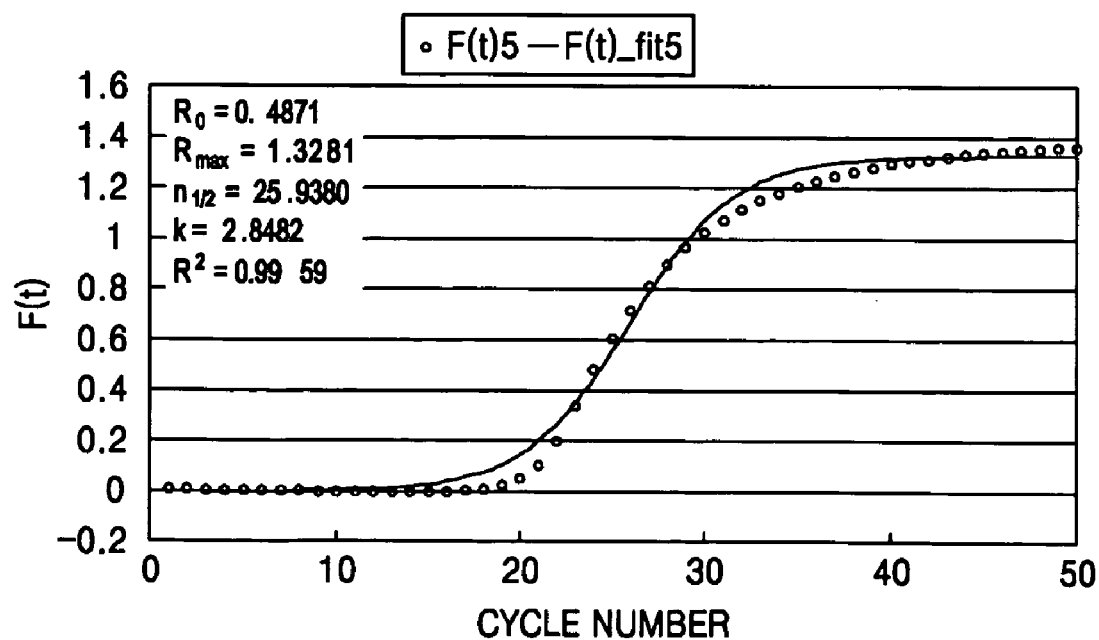
Figure 2F:
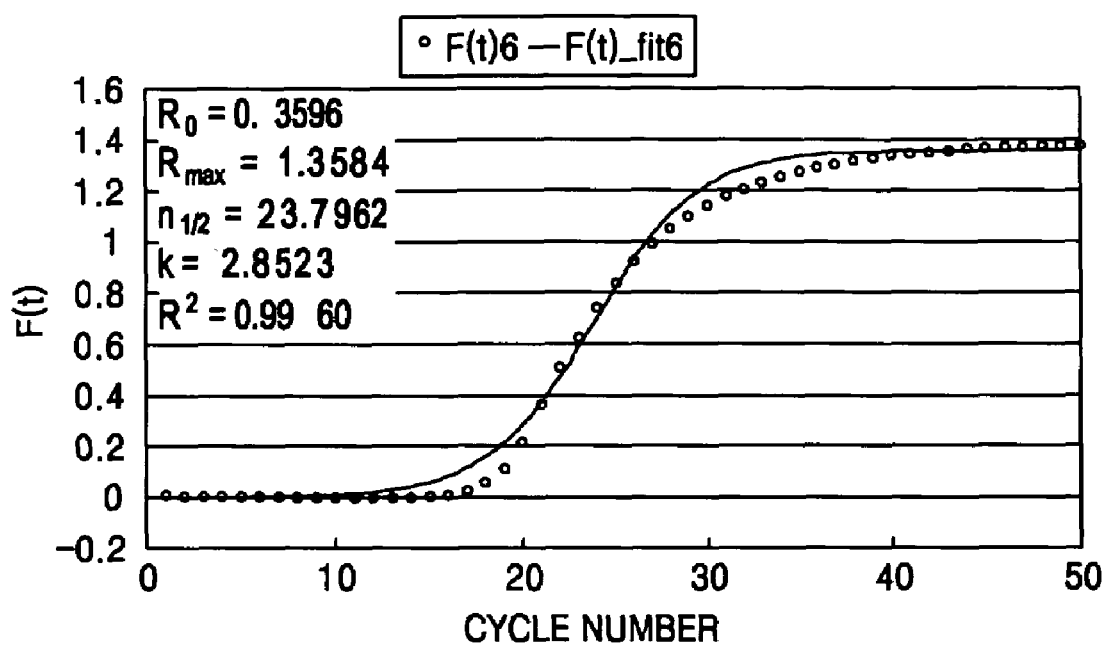

FIG. 2A is the result when the initial concentration of the nucleic acid is $10^7$ copy/rxn (the number of copies in a reaction volume), FIG. 2B is the result when the initial concentration is $10^6$ copy/rxn, FIG. 2C is the result when the initial concentration is $10^5$ copy/rxn, FIG. 2D is the result when the initial concentration is $10^4$ copy/rxn, FIG. 2E is the result when the initial concentration is $10^5$ copy/rxn, and FIG. 2F is the result when the initial concentration is $2.5 \times 10^6$ copy/rxn. It can be seen that the cycle number at which the nucleic acid starts to be rapidly amplified decreases as the initial concentration of the nucleic acid increases.

Also, it can be seen that the graphs of the experimental results about the correlation between the fluorescence intensity of the nucleic acid and the amplification cycle number is almost similar to those of least-square fitting results using the mathematical model of Equation 1.

The amplification efficiency can be modelled as Equations 6a and 6b mathematically.

$$R_n = (1+E_n)R_{n-1} \quad \text{[Equation 6a]}$$

where, $R_n$: the fluorescence intensity at n-th amplification cycle $R_{n-1}$: the fluorescence intensity at (n−1)-th amplification cycle $E_n$: the amplification efficiency at n-th amplification cycle Equation 6a can be rewritten as Equation 6b below.

$$E_n = \frac{R_n - R_{n-1}}{R_{n-1}} \quad \text{[Equation 6b]}$$

Figure 3:
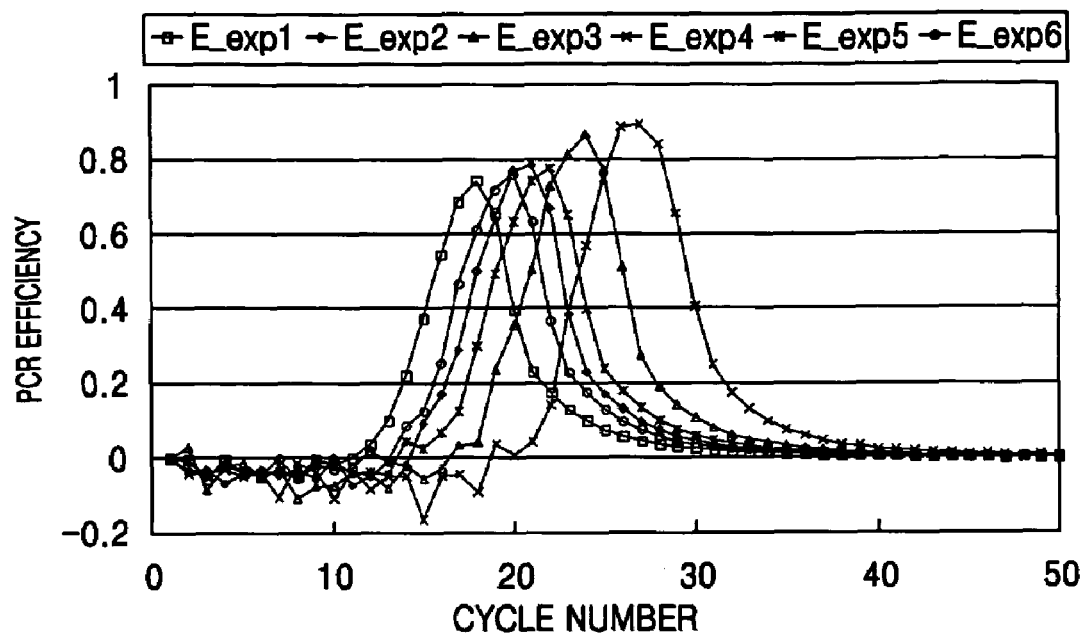
FIG. 3 is a graph showing the relation between amplification efficiency and amplification cycle number for various initial concentrations of a nucleic acid.

FIG. 3 is a graph showing the relation between the amplification efficiency and amplification cycle number for various initial concentrations of the nucleic acid. Referring to FIG. 3, it can be seen that the amplification efficiency is not constant during PCR cycles.

Figure 4:
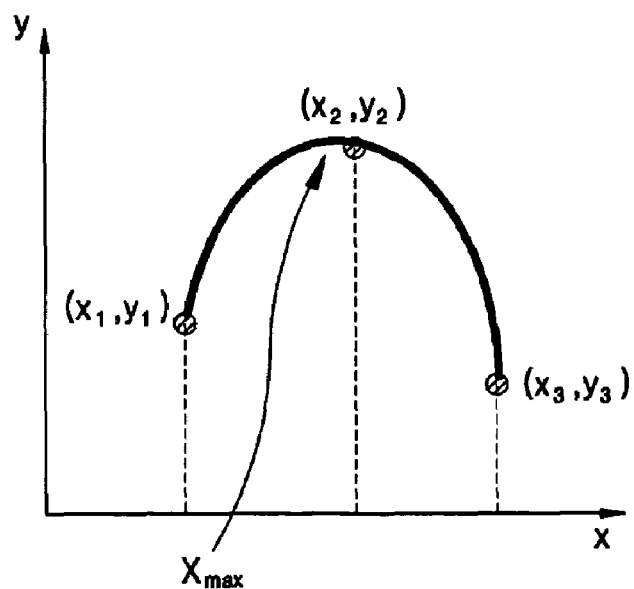
FIG. 4 is a graph showing a method of calculating the characteristic amplification cycle number at which amplification efficiency has the maximum value in FIG. 3.

FIG. 4 is a graph showing a method of finding the characteristic amplification cycle number at which amplification efficiency has the maximum value in FIG. 3.

Referring to FIG. 4, assume that x-y coordinates at three points around the maximum or the minimum are known. The mathematical method of finding the x value which maximizes or minimizes y value using a parabolic curve fitting will now be described.

First, set Equation 7a below for three coordinates $(x_1, y_1)$, $(x_2, y_2)$ and $(x_3, y_3)$.

$$y1=ax_1^2+bx_1+c, \ y2=ax_2^2+bx_2+c, \ y3=ax_3^2+bx_3+c \quad \text{[Equation 7a]}$$

If Equation 7a is rewritten in a matrix form, the result is given by Equation 7b.

$$\begin{pmatrix} x_1^2 & x_1 & 1 \\ x_2^2 & x_2 & 1 \\ x_3^2 & x_3 & 1 \end{pmatrix} \begin{pmatrix} a \\ b \\ c \end{pmatrix} = \begin{pmatrix} y_1 \\ y_2 \\ y_3 \end{pmatrix} \quad \text{[Equation 7b]}$$

If one defines $$\begin{vmatrix} x_1^2 & x_1 & 1 \\ x_2^2 & x_2 & 1 \\ x_3^2 & x_3 & 1 \end{vmatrix} = det(A),$$

constants a, b and c can be represented by Cramer's rule as follows.

$$a = \begin{vmatrix} y_1 & x_1 & 1 \\ y_2 & x_2 & 1 \\ y_3 & x_3 & 1 \end{vmatrix} \Big/ det(A) \quad \text{[Equation 7c]}$$

$$b = \begin{vmatrix} x_1^2 & y_1 & 1 \\ x_2^2 & y_2 & 1 \\ x_3^2 & y_3 & 1 \end{vmatrix} \Big/ det(A)$$

$$c = \begin{vmatrix} x_1^2 & x_1 & y_1 \\ x_2^2 & x_2 & y_2 \\ x_3^2 & x_3 & y_3 \end{vmatrix} \Big/ det(A)$$

Then, $x_{max}$ can be calculated from Equation 7d below.

$$x_{max} = -\frac{b}{2a} = \frac{y_1(x_2^2 - x_3^2) + y_2(x_3^2 - x_1^2) + y_3(x_1^2 + x_2^2)}{2[y_1(x_2 - x_3) + y_2(x_3 - x_1) + y_3(x_1 - x_2)]} \quad \text{[Equation 7d]}$$

Hitherto, the method of implementing the relationships between the fluorescence intensity of the nucleic acid and the amplification cycle number using mathematical models and calculating the parameters of mathematical models have been described. A description will now be made about the relationships between a specific parameter of mathematical models and the initial concentration of the nucleic acid. Also, a description will be made about methods of quantification of the initial concentration of the nucleic acid based on the relationship.

Figure 5:
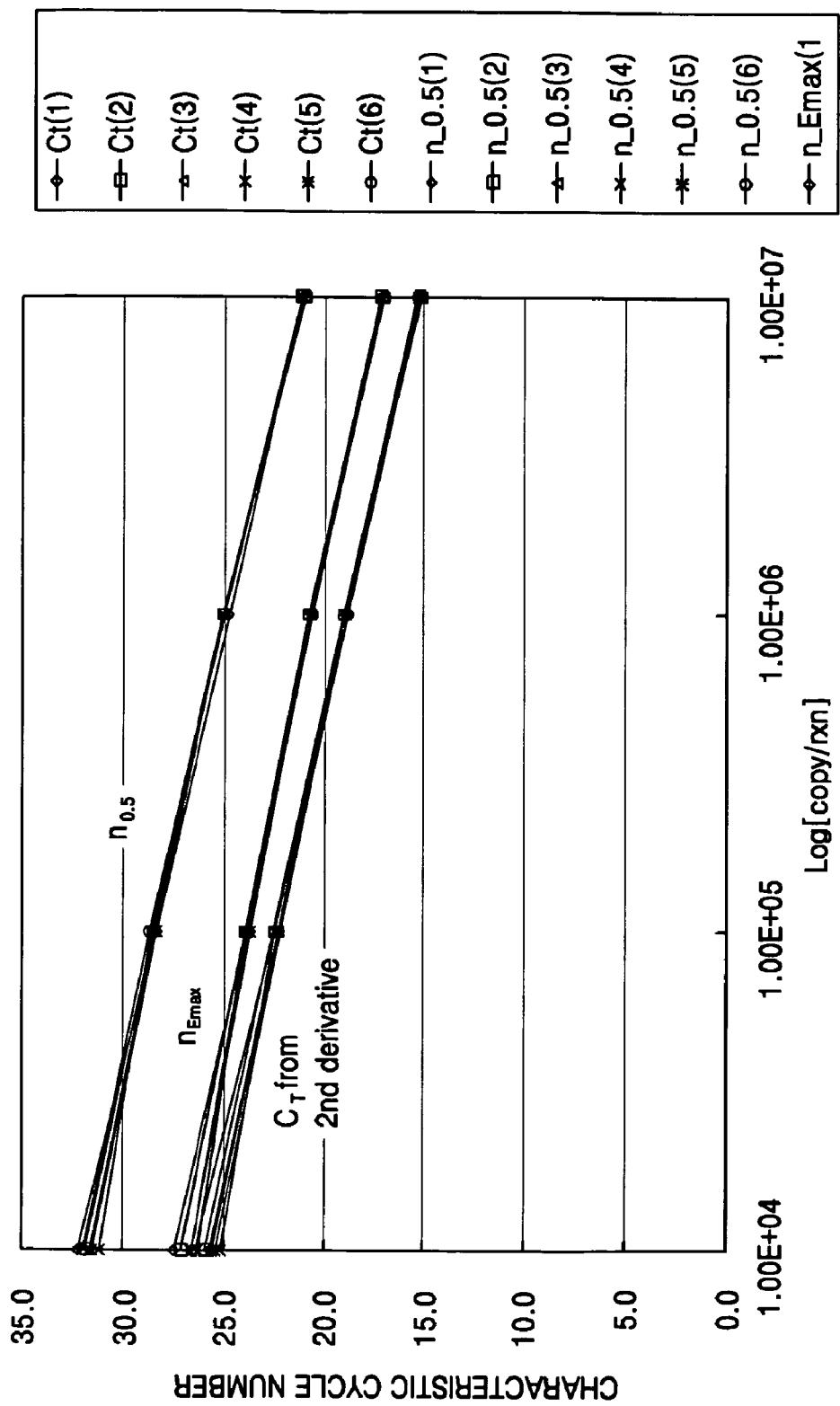
FIG. 5 is a graph showing the relations of the characteristic amplification cycle number ($n_{1/2}$) at which the fluorescence intensity of the nucleic acid subtracted by the background fluorescence intensity of the nucleic acid has half of its maximum value in the mathematical model of FIG. 1 with the initial concentration of the nucleic acid, the characteristic amplification cycle number($n_{Emax}$) at which amplification efficiency has the maximum value in FIG. 3 with the initial concentration of the nucleic acid, and the conventional characteristic amplification cycle number $C_t$ where the $2^{nd}$ derivative of the fluorescence intensity has the maximum value with the initial concentration of the nucleic acid.

FIG. 5 is a graph showing the relations of the characteristic amplification cycle number ($n_{1/2}$) at which the fluorescence intensity of the nucleic acid subtracted by the background fluorescence intensity of the nucleic acid has half of its maximum value in the mathematical model of FIG. 1 with the initial concentration of the nucleic acid, the characteristic amplification cycle number($n_{Emax}$) at whcich the amplification efficiency has the maximum value in FIG. 3 with the initial concentration of the nucleic acid, and the conventional characteristic amplification cycle number $C_t$ at which the $2^{nd}$ derivative of the fluorescence intensity has the maximum value with the initial concentration of the nucleic acid.

Referring to FIG. 5, as the initial concentration (log[copy/rxn]) is higher, both characteristic amplification cycle numbers $n_{1/2}$ and $n_{Emax}$ decrease. Also, it can be seen that the slope of the conventional method of calculating the initial concentration of the nucleic acid using [a] the $2^{nd}$ derivative [value] is almost the same to those using $n_{1/2}$ and $n_{Emax}$, which will be used in this invention. Here, the standard calibration curves using $n_{Emax}$ is placed below those using $n_{1/2}$. Therefore, when $n_{Emax}$ is used, the initial concentration of the nucleic acid can be quantified within a smaller amplification cycle number than the case using $n_{1/2}$.

Figure 6:
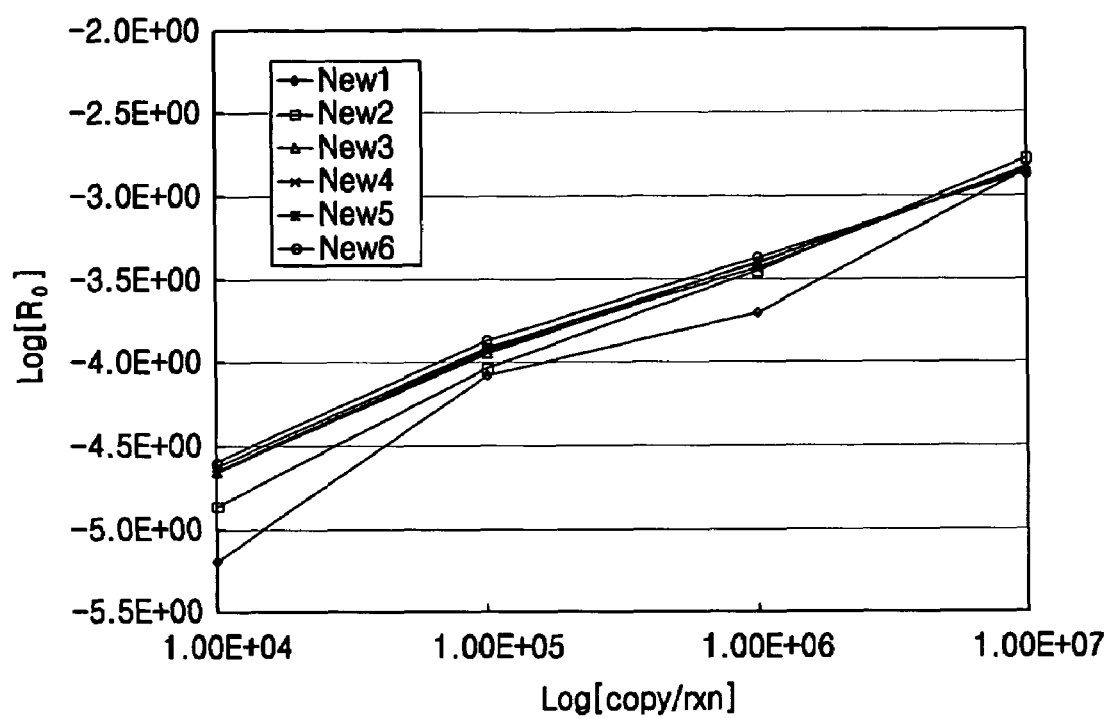
FIG. 6 is a graph showing the relation between $R_0$, the prior-to-amplification fluorescence intensity of the nucleic acid subtracted by a background fluorescence intensity of the nucleic acid in the mathematical model of FIG. 1 and the initial concentration of the nucleic acid.

FIG. 6 is a graph showing the relation between $R_0$ in Equation 5 and the initial concentration of the nucleic acid. Referring to FIG. 6, it can be seen that log (initial concentration of nucleic acid) is linearly proportional to log($R_0$).

Three novel methods are described for obtaining the initial concentration of the nucleic acid using the proportional relationship of FIGS. 5 and 6. The first method is to use the characteristic amplification cycle number or time $n_{1/2}$ at which the fluorescence intensity of the nucleic acid subtracted by the background fluorescence intensity of the nucleic acid has half of its maximum value, and the second method is to use the characteristic amplification cycle number or the characteristic amplification time at which the amplification efficiency of the nucleic acid becomes maximum ($n_{Emax}$) or minimum($n_{Emin}$). The third method is to use $R_0$, the prior-to-amplification fluorescence intensity subtracted by the background fluorescence intensity.

A description will now be made about methods for quantifying the initial concentration of the nucleic acid whose initial concentration is unknown, using the above novel methods.

First, a nucleic acid amplification reaction (for example, PCR, LCR, SDA, NASBA, TMA, RCA, etc.) is performed on predetermined standard nucleic acid samples, whose initial concentrations are known. Then, the parameters of the mathematical model shown in FIG. 1 or 3 are calculated. Then, the standard calibration curve like FIG. 5 or 6, is obtained using a parameter among $n_{1/2}$, $n_{Emax}$ and $R_0$.

Simultaneously, the same nucleic acid amplification reaction is performed on unknown samples and the same parameter($n_{1/2}$ or $n_{Emax}$ or $R_0$) as used in the standard calibration curve is calculated. Then, the initial concentration of the unknown nucleic acid samples [is] are found from the standard calibration curve shown in FIG. 5 or 6. Specifically, when $n_{Emax}$ is used, the amplification efficiency can be obtained and displayed in real time with much less numerical efforts. Moreover, the initial concentration of the nucleic acid can be quantified with a very simple calculation, thereby reducing the number of the amplification cycle number needed to quantify an unknown nucleic acid sample.

FIGS. 7A through 7C are tables showing an example of quantification results of the nucleic acid using the methods in the present invention and those using $C_t$ from the $2^{nd}$ derivative of the fluorescence intensity in the prior art.

FIG. 7A shows the calculated values of parameters used in quantification of the nucleic acid, whose initial concentrations are $10^4$, $10^5$, $10^6$ and $10^7$ copy/rxn so as to obtain the standard calibration curve, as shown in FIGS. 5 and 6. (6 repetitions) FIGS. 7B and 7C show the quantification results of [the] trial nucleic acid samples using the standard calibration curve obtained in FIG. 7A according to the present invention, and those using the standard calibration curve in the prior art. Referring to FIGS. 7B and 7C, instead of Ct, $n_{1/2}$, $n_{Emax}$ or $R_0$ can be used as the characteristic factor for the quantitative analysis of the nucleic acid. In FIG. 7B, Error is the percentage of a value obtained by dividing an absolute value of [(the copy/rxn value calculated from the calibration curve)−(true copy/rxn value)] by (true copy/rxn value). For example, the first value in Error(Ct) is calculated as (5.4E+0.5−5.0E+05)/5.0E+05, i.e., 8.08%. In FIG. 7C, Avg error at 5.0E05 represents an average value of errors in FIG. 7B from 6-time repetitions.

Figure 8:
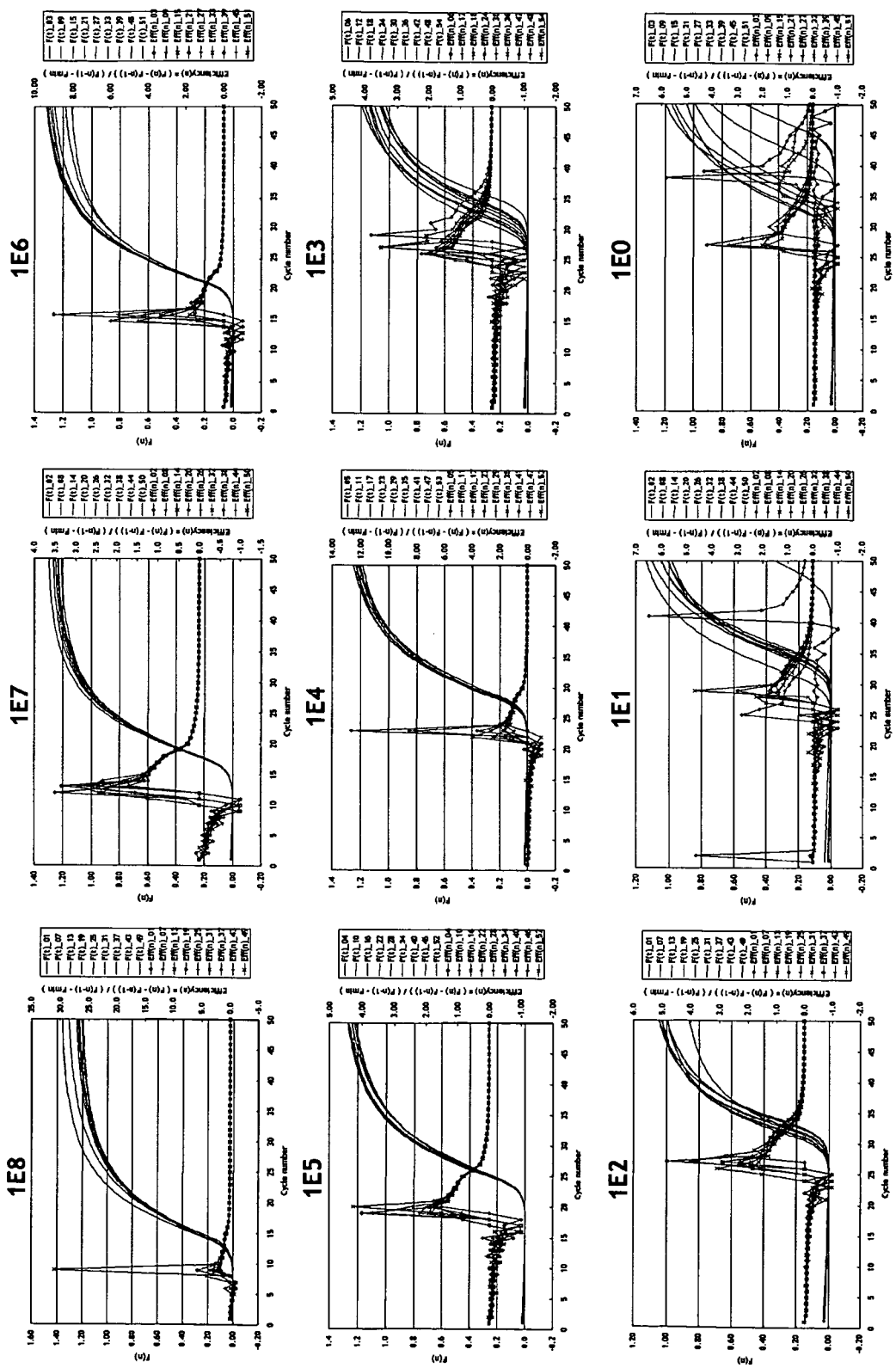
FIG. 8 is graphs showing variations of the relation between fluorescence intensity of a nucleic acid and amplification cycle number, and graphs showing variations of the relation between amplification efficiency and amplification cycle number for various initial concentrations of the nucleic acid.

FIG. 8 shows graphs showing variations of the relation between fluorescence intensity of a nucleic acid and amplification cycle number, and graphs showing variations of the relation between amplification efficiency and amplification cycle number for initial concentrations $10^0$, $10^1$, $10^2$, $10^3$, $10^4$, $10^5$, $10^6$, $10^7$, and $10^8$ copy/rxn of the nucleic acid (9 repetitions).

Figure 11:
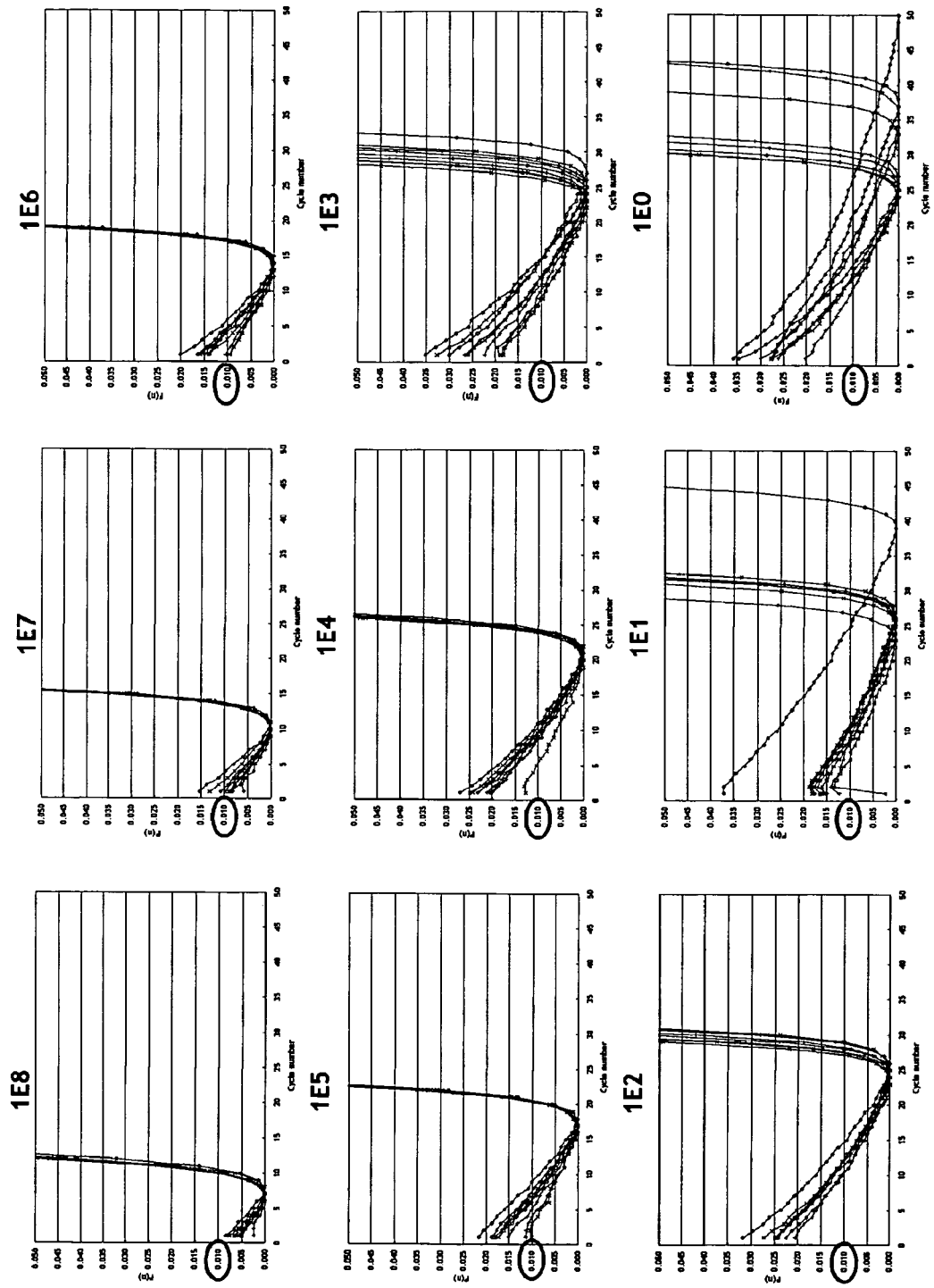
FIG. 11 is a graph showing variations of initial behaviours of fluorescence intensity of a nucleic acid for various initial concentrations.

Referring to FIG. 8, the background fluorescence signals of the nucleic acid are subtracted in the graphs showing the relations between the fluorescence intensity and the amplification cycle number. As can be seen from FIG. 11, the fluorescence intensity starts from a positive value, decreases and again increases at the initial stages. This results from the photobleaching effect, the well-known characteristics of a fluorescence dye. All the minimum fluorescence intensities of FIG. 11 are zero because the background fluorescence intensities are subtracted. This causes the amplification efficiency profiles to have a pointed and sharp maximum as in FIG. 8. The maximum efficiencies in FIG. 8 are larger than 1.0, which cannot be accepted as a concept of efficiency physically.

Figure 9:
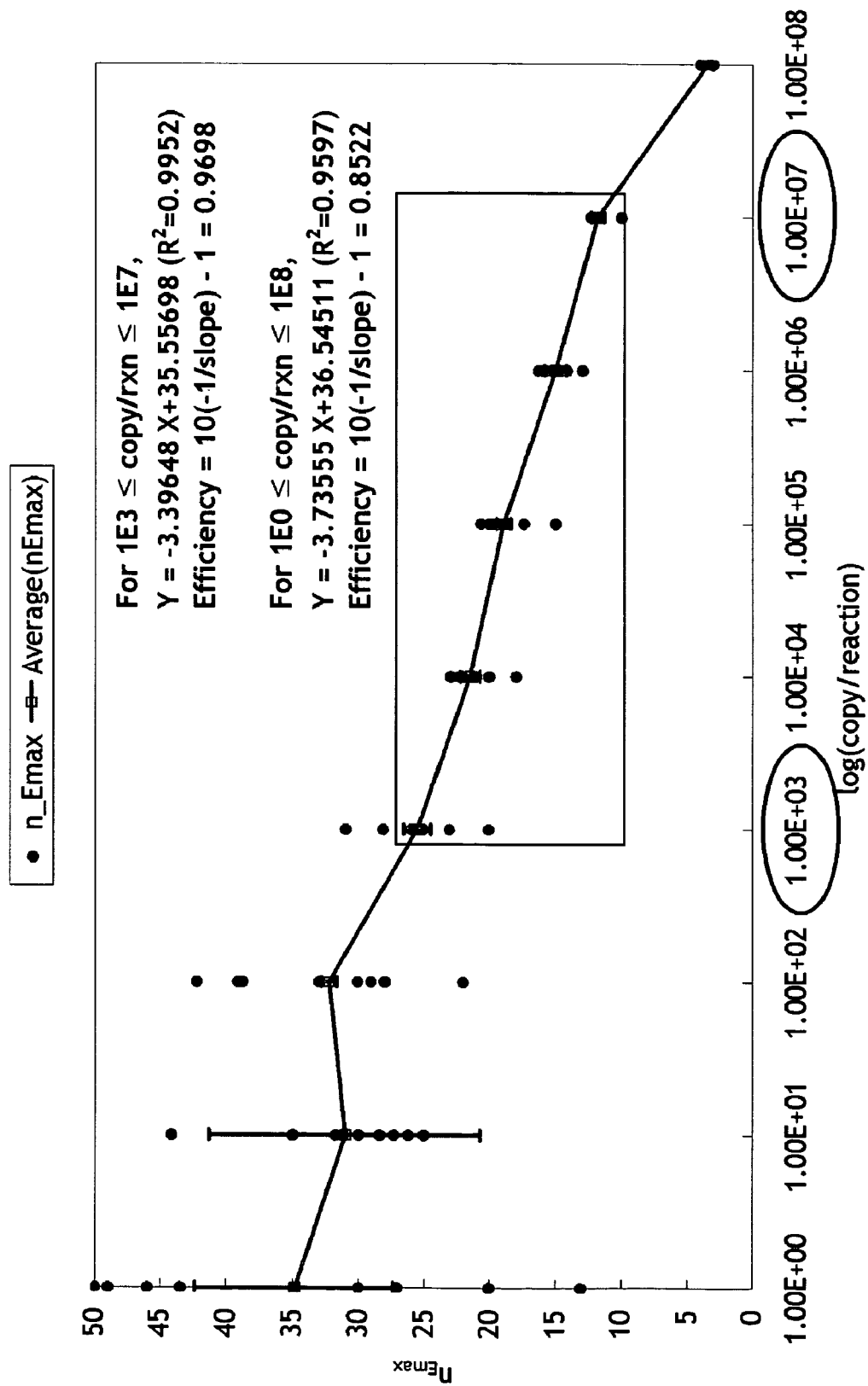
FIG. 9 is a graph showing a relation between the characteristic amplification cycle number at which amplification efficiency has the maximum value and the initial concentration of a nucleic acid obtained from the test results of FIG. 8.

FIG. 9 is a graph which shows the relation between the characteristic amplification cycle number $n_{Emax}$ and the initial concentration of the nucleic acid obtained from the test result of FIG. 8.

Referring to FIG. 9, the graph is linear in range of initial concentration of the nucleic acid from $10^3$ to $10^7$ so that it can be used as a standard calibration curve for that range to calculate the initial concentration according to the present invention. However, when the initial concentration of the nucleic acid is below $10^3$, the data have an irregular pattern.

In order to prevent the amplification efficiency profile from having a pointed and sharp maximum which is larger than 1.0, Equation 6b which represents the amplification efficiency can be rewritten as below.

$$E_n = \frac{(R_n + R_b) - (R_{n-1} + R_b)}{R_{n-1} + R_b} = \frac{R_n - R_{n-1}}{R_{n-1} + R_b} \quad \text{[Equation 8]}$$

where, $R_n$ is the fluorescence intensity in the n-th amplification cycle, $R_{n-1}$ is the fluorescence intensity in the (n−1)-th amplification cycle, $R_b$ is an arbitrary constant which represents the background fluorescence intensity, and $E_n$ is the amplification efficiency in the n-th amplification cycle, respectively.

Figure 10:
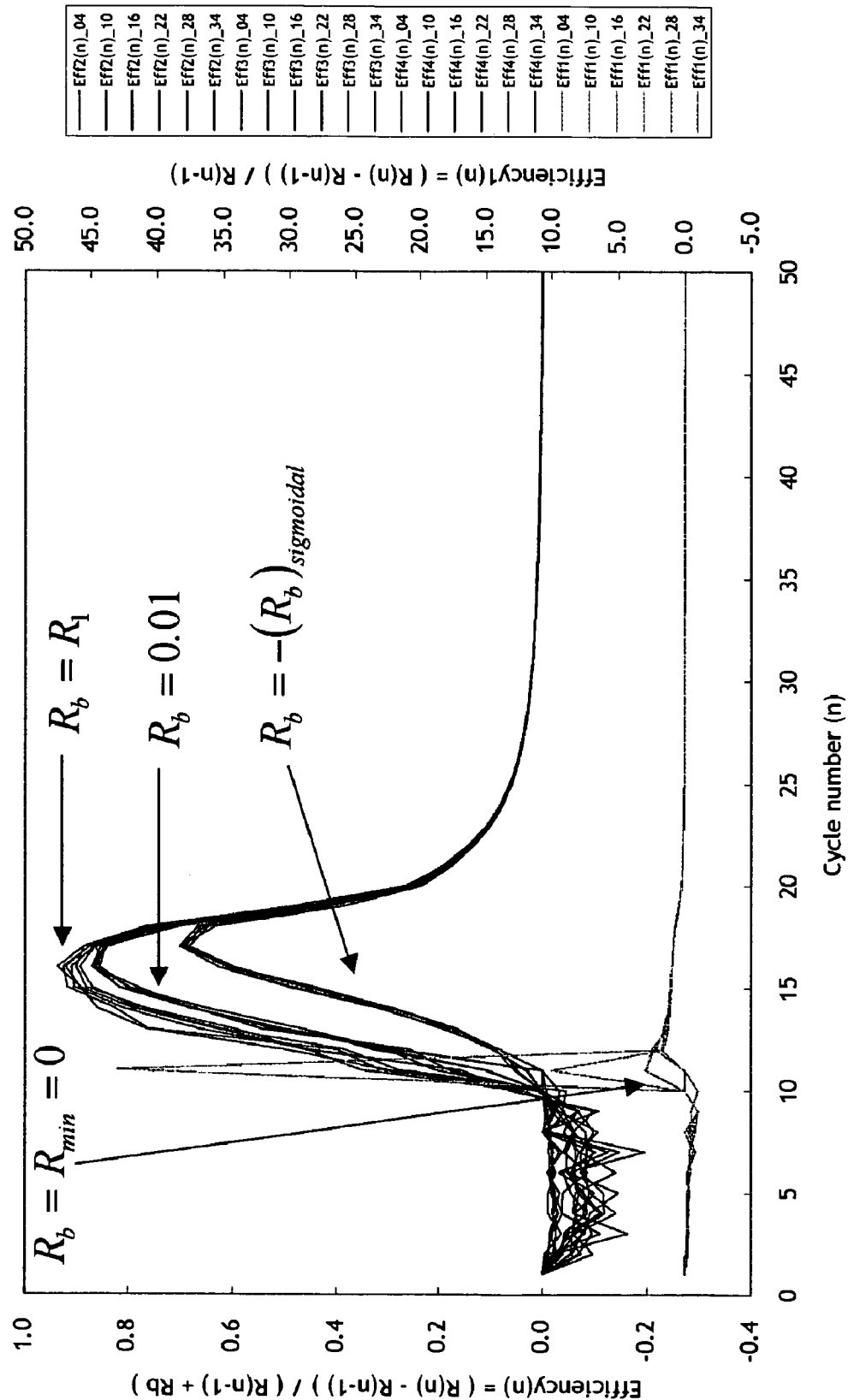
FIG. 10 is a graph showing variations of the relation between background-corrected amplification efficiency and amplification cycle number, adopting various values as the background fluorescence intensity of a nucleic acid.

FIG. 10 is a graph of the background-corrected amplification efficiency profiles according to four different definitions of the background fluorescence intensity $R_b$ in six repetitive tests when the initial concentration of the nucleic acid is $10^7$ copy/rxn. When $R_b$ is zero, that is, when the minimum value $R_{min}$ of the fluorescence intensity during amplification reaction is zero, the amplification efficiency profile has a pointed and sharp shape, as in FIG. 8. Although the amplification cycle numbers at which the maximum amplification efficiency occurs seem almost constant when $R_b$ is zero, it occurs at earlier cycle numbers and its value is not constant for 6 repetitions.

On the contrary, when $R_b$ is non-zero (that is, $R_1$, 0.01, $-(R_b)_{sigmoidal}$), the amplification cycle numbers at which the maximum amplification efficiency occurs seem almost constant and the value of the maximum amplification efficiency is also constant for 6 repetitions.

The constant acceptable as the constant $R_b$ and the improvement when $R_b$ is considered in the definition of the amplification efficiency will now be described with reference to FIGS. 15 through 17.

First, $-(R_b)_{sigmoidal}$, which results from the least-square fitting of the fluorescence intensity data at all amplification cycles to sigmoidal model in Equation 1, can be used as $R_b$ in Equation 8.

Second, when the fluorescence intensity starts from non-zero, decreases to zero and again increases (refer to FIG. 11) at the initial stage of amplification reaction, the value corresponding to the initial fluorescence intensity can be used as the value of $R_b$. For example, referring to FIG. 11, although the initial fluorescence intensity is slightly different for different initial concentrations of the nucleic acid, it is 0.01 on average. Therefore, the value of 0.01 can be used as the value of $R_b$. The initial fluorescence intensity will not change significantly if the amplification conditions such as reagents, fluorescence dyes, and optical exposure time do not change. Therefore, once the value corresponding to the initial fluorescence intensity is determined experimentally, it can be used as $R_b$ from that time on. On the contrary, if the amplification conditions such as reagents, fluorescence dyes, and optical exposure time change, the value corresponding to the initial fluorescence intensity must be determined again experimentally.

Third, the fluorescence intensity at the first amplification cycle, $R_1$ can be used as the value of $R_b$. Even though the amplification conditions such as reagents, fluorescence dyes, and optical exposure time change, this method has the advantage that users need no additional efforts for determining $R_b$ because the fluorescence intensity at the first amplification cycle is always measured at every test. Although this method has this advantage over the second method, the quantification error may increase when the fluorescence intensity at the first amplification cycle is very close to zero.

Fourth, the value that makes the maximum amplification efficiency be "1" (unity) in the amplification efficiency function of Equation 8 can be used as the value of $R_b$. In order to obtain $R_b$ such that the maximum amplification efficiency is "1", the value of $R_b$ has to be found by iterative methods such as successive substitution at every amplification experiment. Although this method is ideal in principle, the iterative calculation may be complicated or time-consuming.

As described above, the background fluorescence intensity $R_b$ can be set to one of the following values: 1) $-(R_b)_{sigmoidal}$ obtained through the least-square fitting of the fluorescence intensity data at all amplification cycles to the sigmoidal model in Equation 1; 2) the value (about 0.01 for FIG. 11) corresponding to the initial fluorescence intensity; 3) [the strength $R_1$ of] the fluorescence intensity at the first amplification cycle, $R_1$; and 4) the value that makes the maximum amplification efficiency be "1".

Here, the use of $-(R_b)_{sigmoidal}$ of the background fluorescence intensity may be inconvenient because it must be calculated through the nonlinear curve fitting of sigmoidal model. However, other methods in the present invention (the initial fluorescence intensity, $R_1$, and the value that makes the maximum amplification efficiency be "1") need not use the curve fitting.

Even a larger positive or negative value can be used as the value of $R_b$ for calculating the background-corrected amplification efficiency. This will be described with reference to FIGS. 12A through 12C.

Figure 12A:
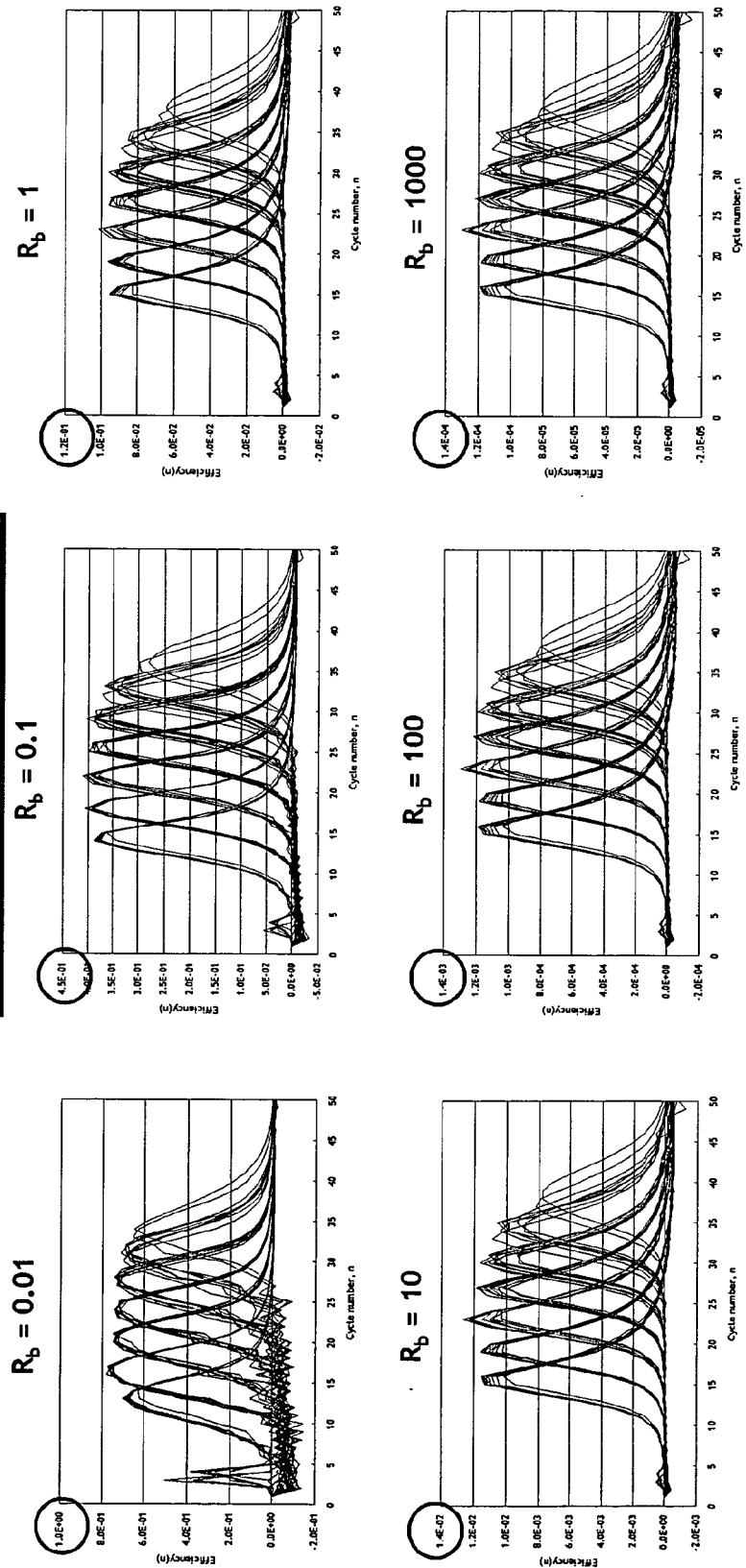
FIGS. 12A and 12B are graphs showing variations of the background-corrected amplification efficiency profiles for various initial concentrations of a nucleic acid adopting various values as the background fluorescence intensity.
Figure 12B:
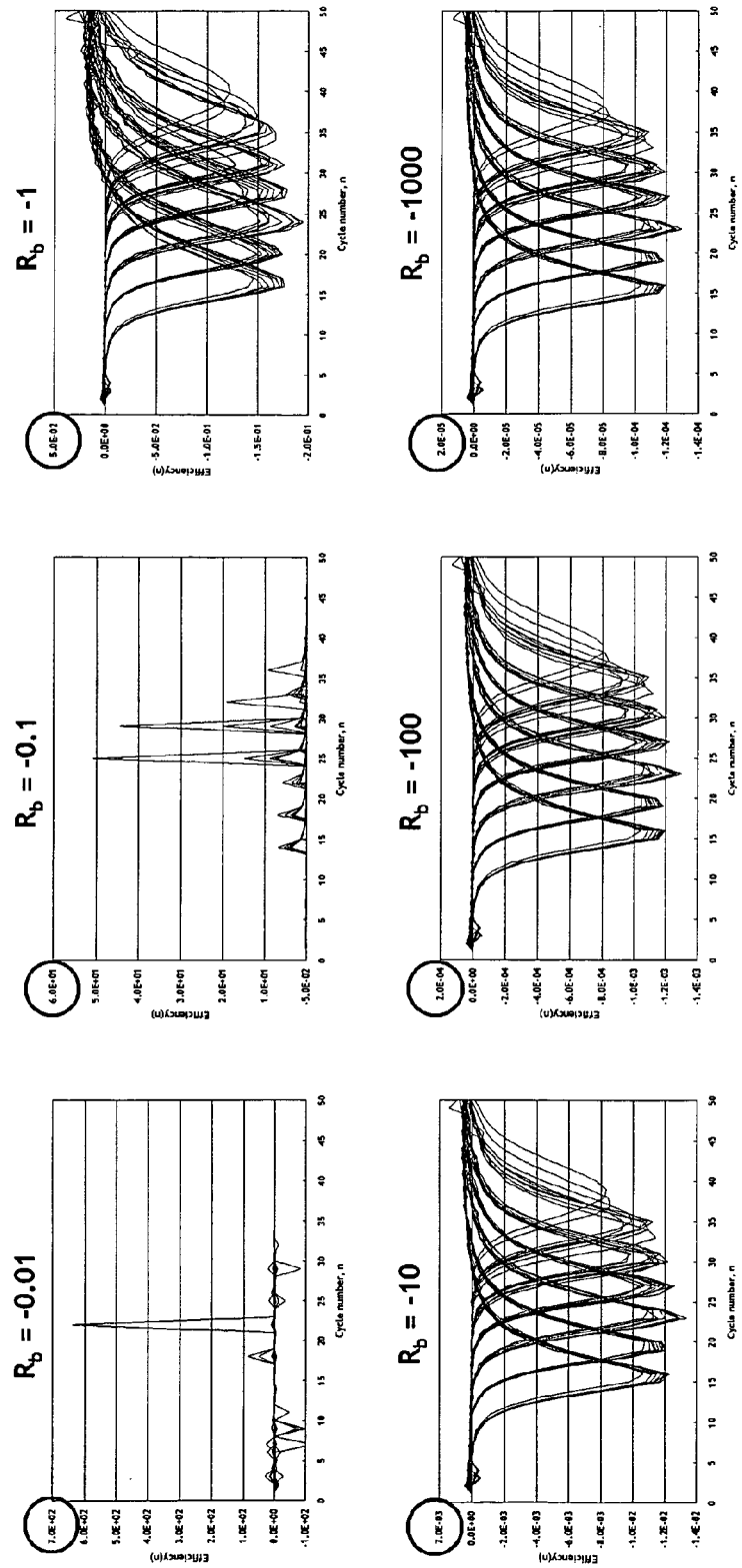

FIGS. 12A and 12B are graphs illustrating variations of the background-corrected amplification efficiency for various values of the background fluorescence intensity using the same experimental data as in FIG. 8.

The cases where $R_b$ are positive values of 0.01, 0.1, 1, 10, 100, and 1000 are shown in FIG. 12A. Since the respective cases have well-distinguishable positive peaks in background-corrected amplification efficiency with almost an equal interval in amplification cycle number according to the initial concentration of the nucleic acid, they can be used to quantify the initial concentration of the nucleic acid according to the present invention. However, when the value of $R_b$ is larger than 0.1, the maximum value of the background-corrected amplification efficiency becomes very smaller than 1, which has no physical meaning in terms of the amplification efficiency. However, as can be seen from FIG. 12A, the amplification cycles $n_{Emax}$ where the respective background-corrected amplification efficiency profiles have the maximum values are located at almost an equal interval. Thus, all of them can be used in qualifying the initial concentration of the nucleic acid. However, it is preferable to use the case where the background-corrected amplification efficiency is in range from 0 to 1, that is, the case where the value of $R_b$ is 0.01 (the value corresponding to the initial fluorescence intensity of the nucleic acid).

The cases where $R_b$ are negative values of $-0.01, -0.1, -1, -10, -100$, and $-1000$ are shown in FIG. 12B. When the value of $R_b$ is $-0.01$ and $-0.1$, the divisor of the background-corrected amplification efficiency function (Equation 8) approaches to zero very closely, so that the background-corrected amplification efficiency profiles have a pointed and sharp peaks and do not represent the regular-interval pattern when the absolute value of $R_b$ is large, the background-corrected amplification efficiency profiles have well-distinguishable negative peaks with almost an equal interval in amplification cycle number according to the initial concentration of the nucleic acid. Specifically, when the value of $R_b$ is less than $-1$, the value of the background-corrected amplification efficiency is negative. Since the amplification efficiency has the physical meaning only in the range from 0 to 1, although the initial concentration of the nucleic acid can be quantified using the values given in FIG. 12B, there is no physical meaning in terms of the amplification efficiency. However, as can be seen from FIG. 12B, when the value of $R_b$ is less than $-1$ (e.g., $-1, -10, -100, -1000$), the amplification cycles $n_{Emin}$ where the respective background-corrected amplification efficiency profiles have the minimum values are located at almost an equal interval. Thus, all of them can be used in qualifying the initial concentration of the nucleic acid.

Figure 12C:
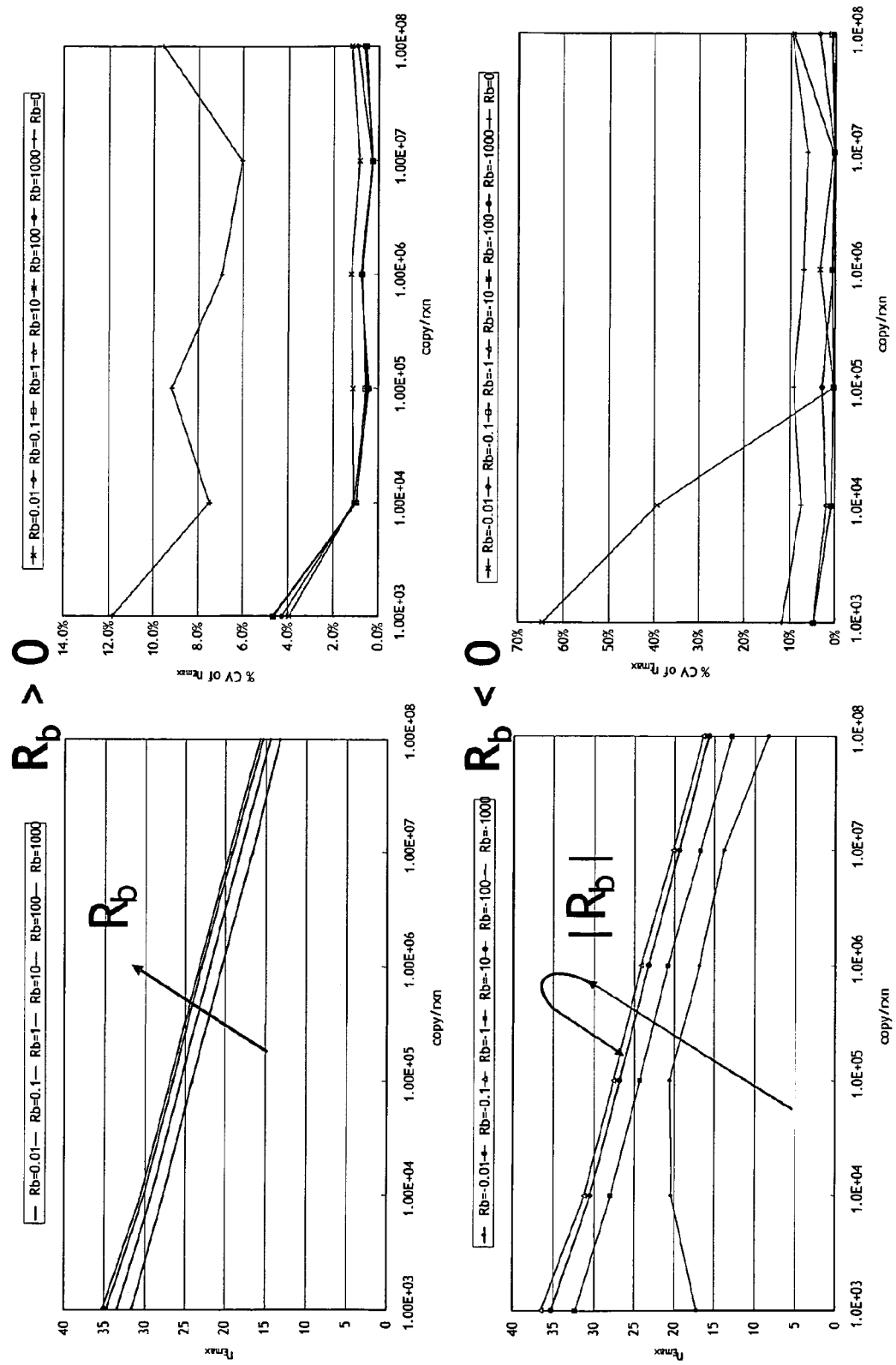
FIG. 12C shows graphs of variations of the relation between the initial concentration of a nucleic acid and the characteristic amplification cycle number where the background-corrected amplification efficiency has the maximum or the minimum value, and graphs of variations of the relation between the initial concentration of a nucleic acid and % CV of the characteristic amplification cycle number where the background-corrected amplification efficiency has the maximum or the minimum value for various values of $R_b$ in FIGS. 12A and 12B.

FIG. 12C shows graphs of variations of the relation between the initial concentration of the nucleic acid and the characteristic amplification cycle number $n_{Emax}$ or $n_{Emin}$ where the background-corrected amplification efficiency has the maximum or the minimum value, and graphs of variations of the relation between the initial concentration of a nucleic acid and % CV of $n_{Emax}$ or $n_{Emin}$ for various values of $R_b$ in FIGS. 12A and 12B.

Referring to FIG. 12C, when the value of $R_b$ increases to a positive value (FIG. 12A) or decreases to a negative value (FIG. 12B), the graphs of the relation between the initial concentration of the nucleic acid and $n_{Emax}$ or $n_{Emin}$ converge to a curve, respectively. Except the case where the value of $R_b$ is 0 and −0.01, % CV of $n_{Emax}$ is within 5% when the initial concentration of the nucleic acid is in range from $10^3$ to $10^8$ copy/rxn. A relation between the quantification error in the initial concentration of the nucleic acid and % CV of $n_{Emax}$ or $n_{Emin}$ will be described with reference to FIG. 17.

When the value of $R_b$ is larger than some value, the value of % CV does not almost change. Thus, the values except $R_b$=0 in FIG. 10, that is, $R_1$, 0.01, and $-(R_b)_{sigmoidal}$ may be preferably used as the value of $R_b$ so as to improve % CV of $n_{Emax}$ while the amplification efficiency is in range from 0 to 1.

Figure 13:
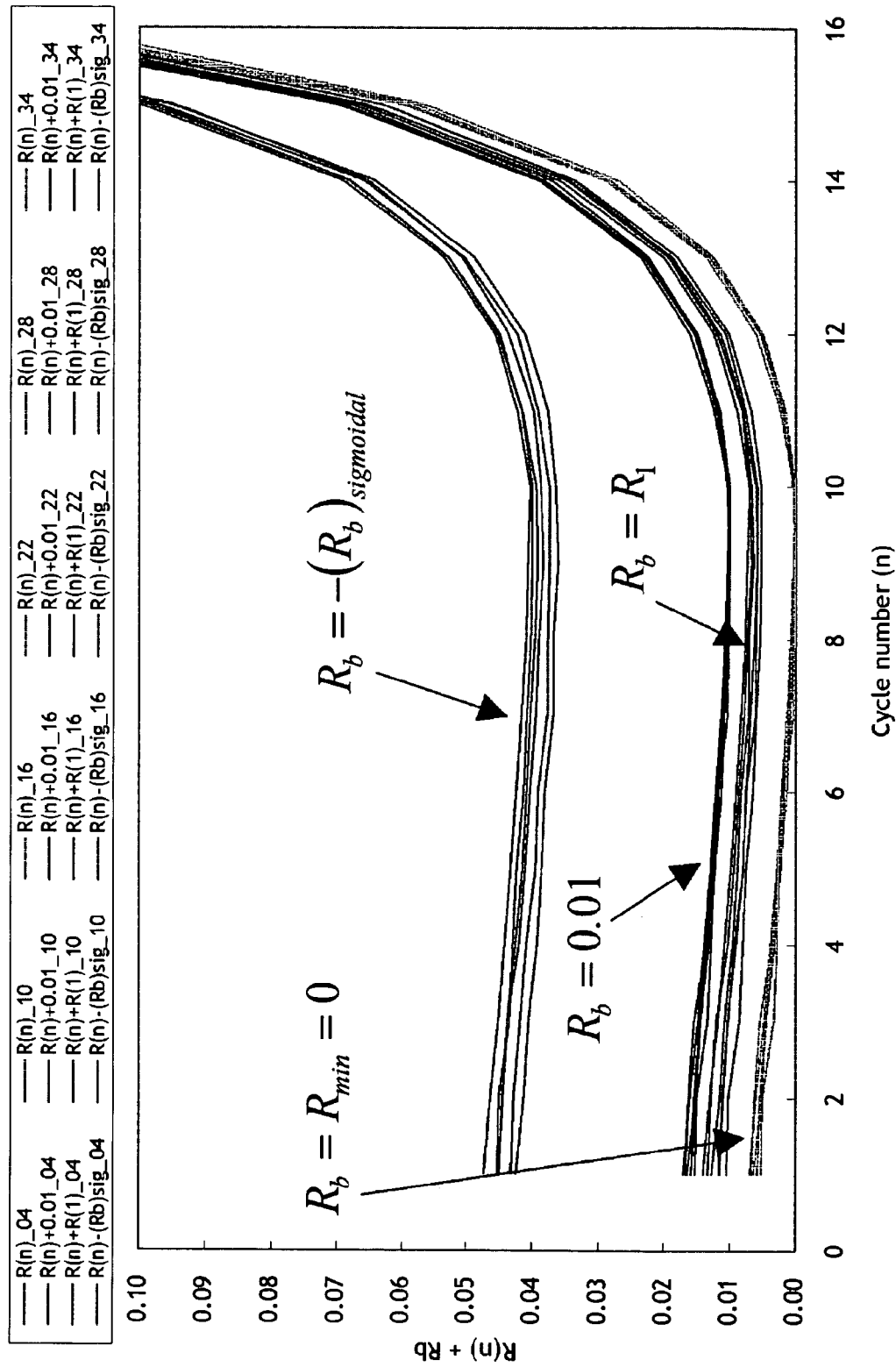
FIG. 13 is a graph showing variations of the relations between fluorescence intensity and amplification cycle number for various methods of adopting the background fluorescence intensity.

FIG. 13 is a graph showing variations of the relations between fluorescence intensity and amplification cycle number for various methods of adopting the background fluorescence intensity.

Figure 14:
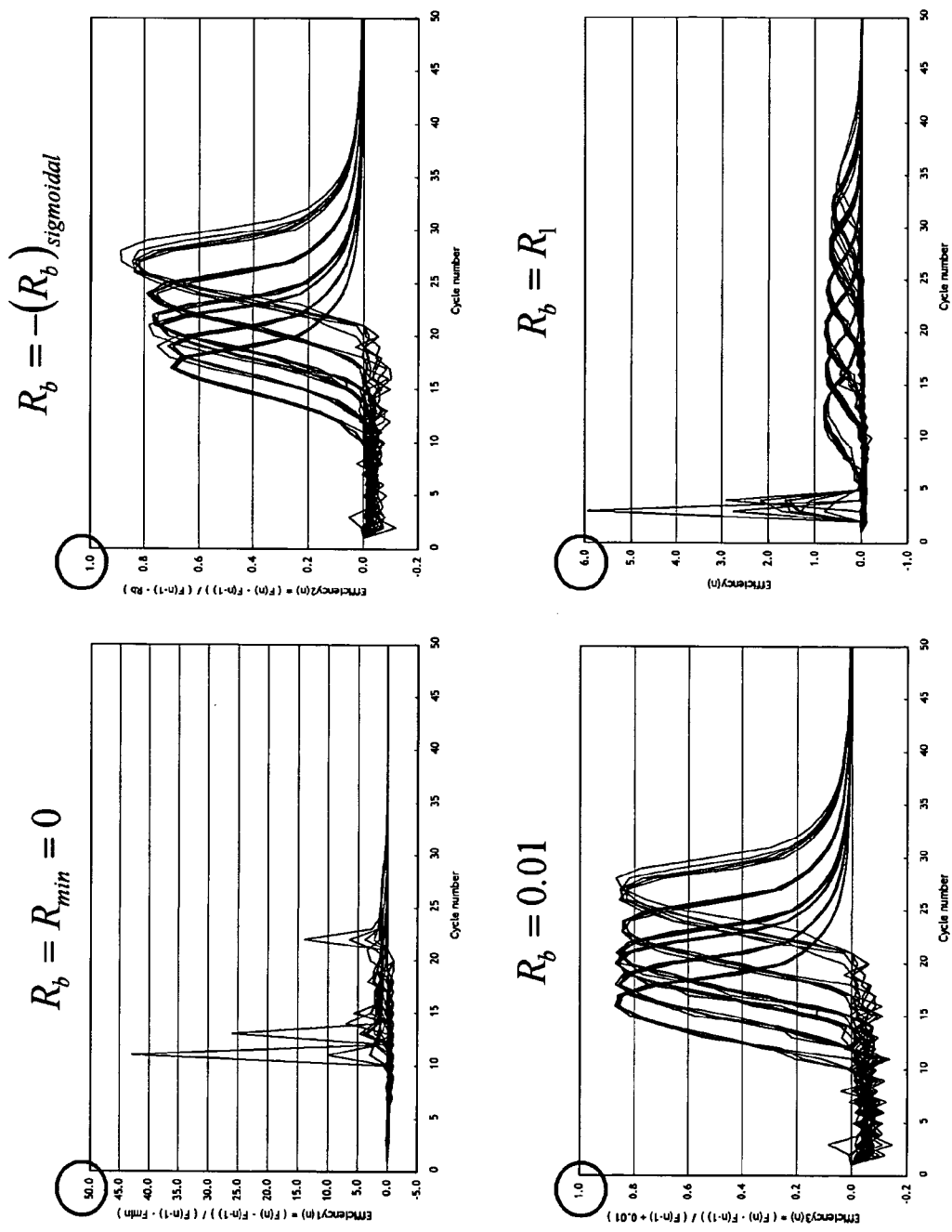
FIG. 14 shows graphs showing variations of the relations between the background-corrected amplification efficiency and amplification cycle number for various methods of adopting the background fluorescence intensity in FIG. 13.

FIG. 14 shows graphs showing variations of the relations between the background-corrected amplification efficiency and amplification cycle number for various methods of adopting the background fluorescence intensity in FIG. 13.

Referring to FIGS. 13 and 14, when the value of $R_b$ is zero, which is the minimum value of the fluorescence intensity profiles (that is, $R_b = R_{bmin} = 0$), so that the divisor $(R^{n-1} + R_b)$ of Equation 8 approaches to zero. Thus, the amplification efficiency $E_n$ increases too large and $E_{max}$ peak becomes sharp and pointed. Also, the amplification efficiency may be easily influenced by noise. When the value of $R_b$ is non-zero, the amplification efficiency profiles have well-distinguishable peaks with almost an equal interval in amplification cycle number according to the initial concentration of the nucleic acid. However, in FIG. 14, if $R_b = R^1$, the maximum values of the background-corrected amplification efficiency are larger than 1 in the initial stage of the amplification cycle (cycle number≦5) and the shape of the peaks are very sharp and pointed. In the conventional method of amplifying the nucleic acid, this rapid amplification in this early stage generally does not occur and the amplification efficiency of larger than 1 has no physical meaning. Therefore, these peaks have to be ignored and the second maximum peaks could be used for quantification of the initial concentration of the nucleic acid.

Figure 15:
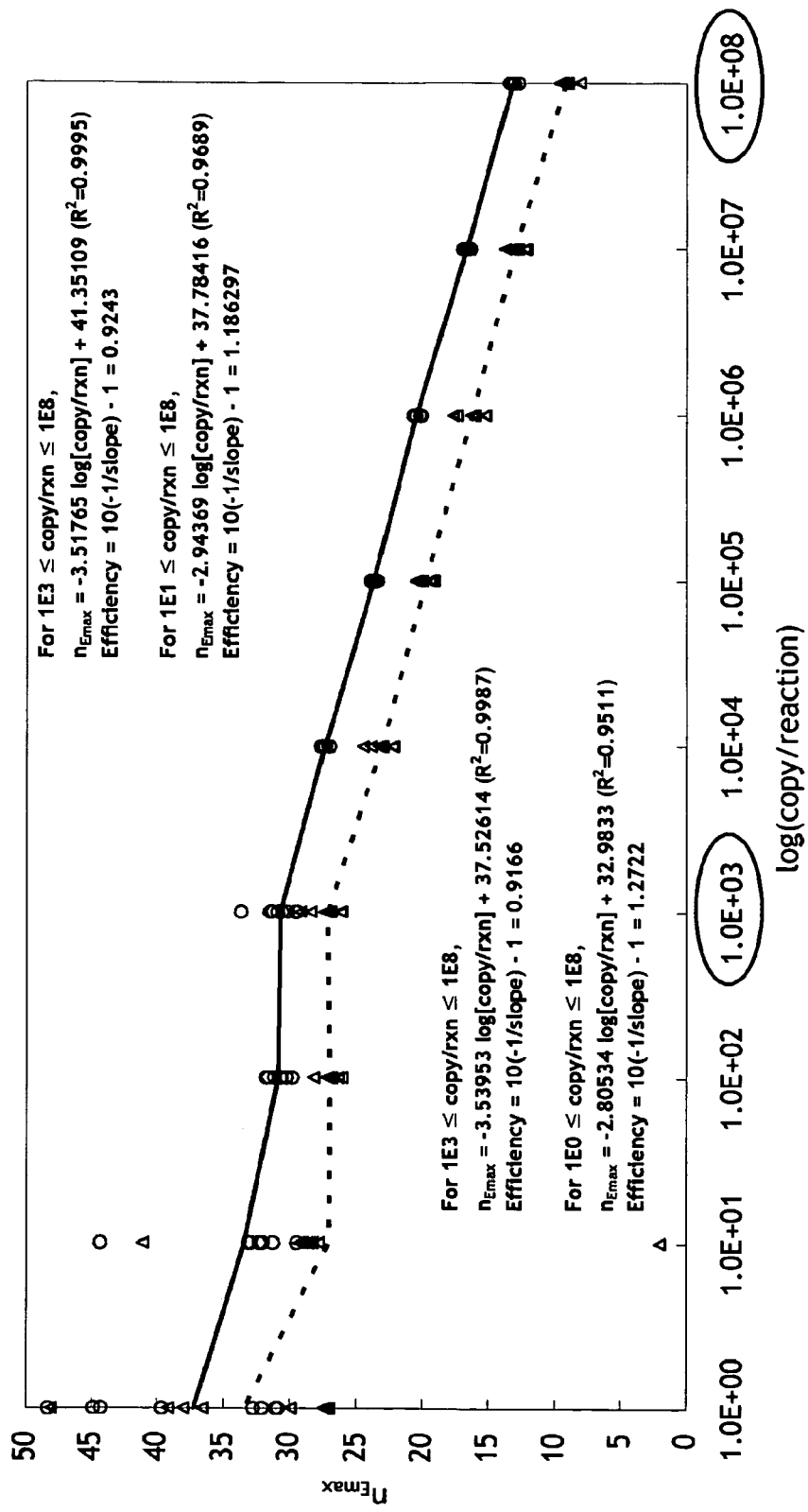
FIG. 15 is a graph showing the relations between the initial concentration of a nucleic acid and characteristic amplification cycle number where the background-corrected amplification efficiency has the maximum value with and without background fluorescence intensity correction.

FIG. 15 is a graph showing the standard calibration curves between the initial concentration of the nucleic acid and the characteristic amplification cycle number $n_{Emax}$ with ($R_b$=0.01) and without ($R_b$=0) the background fluorescence intensity correction.

Referring to FIG. 15, both standard calibration curves (with and without the background fluorescence correction) are linear in the initial concentration of the nucleic acid ranging from $10^3$ to $10^8$. [The latter graph is disposed above the former graph.] It is seen that he standard calibration curve with background fluorescence correction is located above that without background fluorescence correction.

Figure 16:
FIG. 16 shows the effect of background fluorescence intensity correction on the accuracy of the quantification method of the initial concentration of a nucleic acid using the characteristic amplification cycle number where the background-corrected amplification efficiency has the maximum value, which is obtained using the relations of FIG. 15.

FIG. 16 shows the effect of background fluorescence intensity correction on the accuracy of the quantification method of the initial concentration of the nucleic acid using the characteristic amplification cycle number $n_{Emax}$, which is obtained using the standard calibration curve of FIG. 15.

As can be seen from FIG. 16, using the background fluorescence correction ($R_b$=0.01), % CV (=St.Dev(standard deviation)/Avg(average) of $n_{Emax}$ is reduced remarkably.

Figure 17:
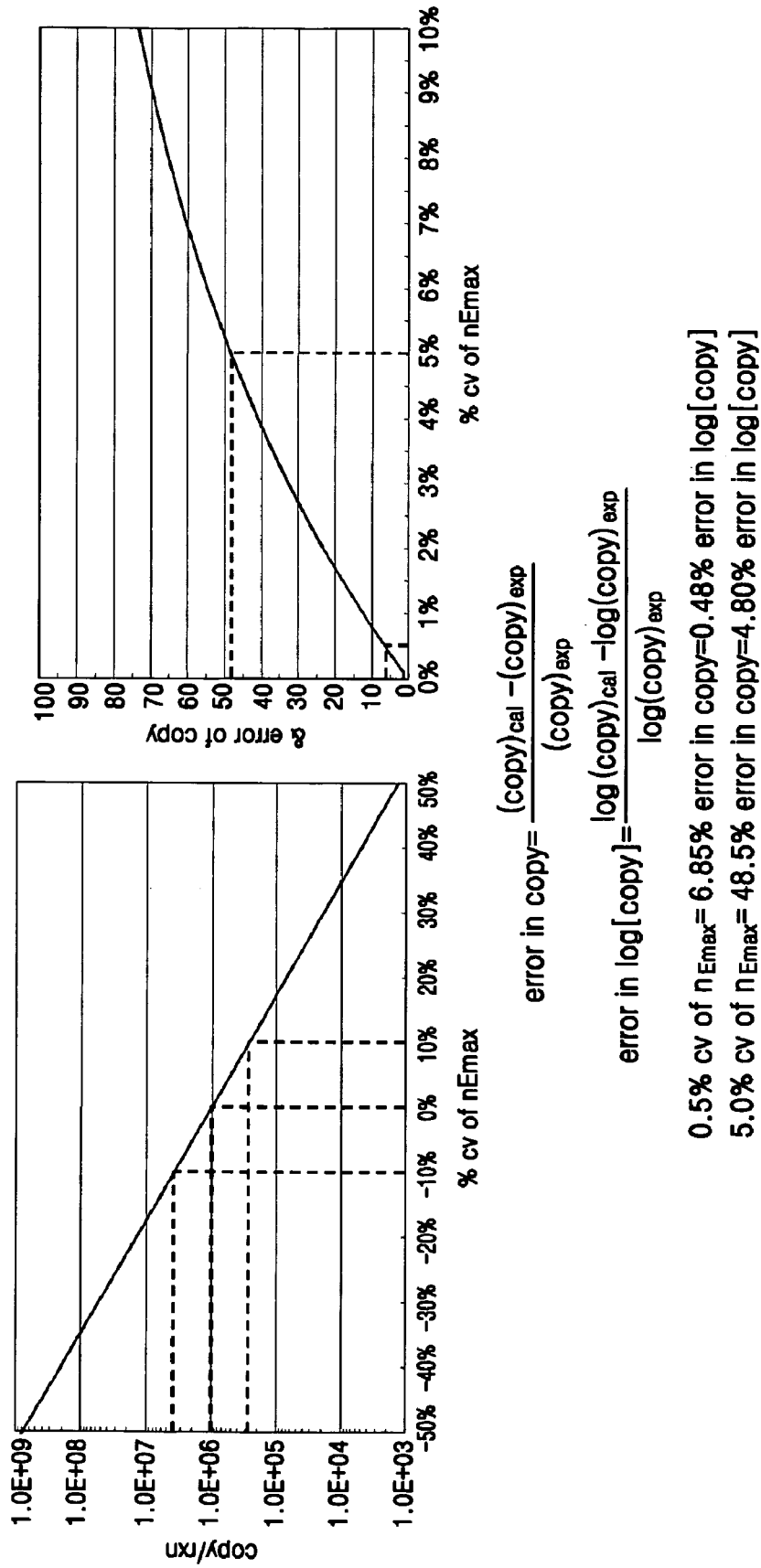
FIG. 17 is a graph showing an example illustrating the effect of % CV of the characteristic amplification cycle number on the accuracy of quantification of the initial concentration of a nucleic acid.

FIG. 17 is a graph showing an example illustrating the effect of % CV of the characteristic amplification cycle number on the accuracy of quantification of the initial concentration of a nucleic acid.

Referring to FIG. 17, when % CV of the characteristic amplification cycles changes from 0.5 to 5.0, the error (in copy) greatly changes from 6.85% to 48.5%. That is, even a slight increase in the error of the characteristic amplification cycle may cause a large error in the quantification results of the initial concentration of the nucleic acid. For these reasons, a very accurate quantifying method is indispensable. As shown in FIG. 16, using the background fluorescence correction ($R_b$=0.01), the % CV of $n_{Emax}$ is greatly reduced so that the quantification accuracy is greatly improved compared with the case without using the background fluorescence correction ($R_b$=0).

According to the present invention, three novel methods for finding the initial concentration of the nucleic acid from the real-time nucleic acid amplification (PCR, LCR, SDA, NASBA, TMA, RCA, etc.) data are described using the characteristic amplification cycle number or time at which the fluorescence intensity of the nucleic acid subtracted by the background fluorescence intensity of the nucleic acid has half of its maximum value, the characteristic amplification cycle number or time at which the amplification efficiency has the maximum or the minimum value, and the prior-to-amplification fluorescence intensity subtracted by the background fluorescence intensity, based on the mathematical model with respect to the correlation between the amplification amount of the nucleic acid and the amplification cycle, without differentiation or integration.

Specifically, when the characteristic amplification cycle at which the amplification efficiency has the maximum or the minimum value is used, the amplification efficiency can be obtained and displayed in real time with much less numerical efforts from the real-time nucleic acid amplification data. Therefore, the initial concentration of the nucleic acid can be found more rapidly than other methods.

The invention can also be embodied as computer readable codes on a computer-readable recording medium. The computer-readable recording medium is any data storage device that can store data which can be thereafter read by a computer system. Examples of the computer-readable recording medium include read-only memory (ROM), random-access memory (RAM), CD-ROMs, magnetic tapes, floppy disks, optical data storage devices, and carrier waves (such as data transmission through the Internet). The computer-readable recording medium can also be distributed over network coupled computer systems so that the computer readable code is stored and executed in a distribution fashion.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for quantifying an initial concentration of a nucleic acid, comprising:
    amplifying a nucleic acid;
    producing a function representing a correlation between a fluorescence intensity which increases or decreases in proportion to an amount of the nucleic acid and an amplification cycle number or an amplification time of the nucleic acid;
    using the function to calculate a characteristic amplification cycle number or a characteristic amplification time at which the fluorescence intensity of the nucleic acid subtracted by a background fluorescence intensity of the nucleic acid has half of maximum value of the fluorescence intensity;

calculating the initial concentration of the nucleic acid from the characteristic amplification cycle number or the characteristic amplification time; and providing results of the calculation of the initial concentration to a user.

2. The method of claim 1, wherein the nucleic acid is amplified using enzyme.

3. The method of claim 1, wherein the nucleic acid is amplified using a nucleic acid amplification method that requires a thermal cycling.

4. The method of claim 1, wherein the nucleic acid is amplified using an isothermal nucleic acid amplification method.

5. The method of claim 1, wherein the function representing the correlation is produced using a sigmoidal model.

6. The method of claim 5, wherein the characteristic amplification cycle number or the characteristic amplification time at which the fluorescence intensity of the nucleic acid subtracted by the background fluorescence intensity of the nucleic acid has half of maximum value of the fluorescence intensity is calculated using a nonlinear least-square fitting method with respect to the function that uses the sigmoidal model.

7. The method of claim 1, wherein the initial concentration of the nucleic acid is calculated from the characteristic amplification cycle number or the characteristic amplification time by using a standard calibration curve, which represents a relationship between the initial concentration of the nucleic acid and the characteristic amplification cycle number or the characteristic amplification time at which the fluorescence intensity of the nucleic acid subtracted by the background fluorescence intensity of the nucleic acid has half of its maximum value.

* * * * *